(12) United States Patent
Hantash et al.

(10) Patent No.: US 8,208,189 B2
(45) Date of Patent: Jun. 26, 2012

(54) TREATMENT OF ALOPECIA BY MICROPORE DELIVERY OF STEM CELLS

(75) Inventors: Basil M. Hantash, East Palo Alto, CA (US); George Frangineas, Fremont, CA (US); Leonard C. DeBenedictis, Palo Alto, CA (US)

(73) Assignee: Reliant Technologies, Inc., Mountain View, CA (US)

( * ) Notice: Subject to any disclaimer, the term of this patent is extended or adjusted under 35 U.S.C. 154(b) by 1085 days.

(21) Appl. No.: 12/102,739

(22) Filed: Apr. 14, 2008

(65) Prior Publication Data

US 2008/0254006 A1     Oct. 16, 2008

Related U.S. Application Data

(60) Provisional application No. 60/911,796, filed on Apr. 13, 2007.

(51) Int. Cl.
*G02B 26/08* (2006.01)
*G02B 26/10* (2006.01)
*G02B 26/12* (2006.01)
(52) U.S. Cl. ............... 359/205.1; 359/212.1; 359/216.1
(58) Field of Classification Search ............... 359/205.1, 359/212.1, 216.1
See application file for complete search history.

(56) References Cited

U.S. PATENT DOCUMENTS

| 7,372,606 | B2 | 5/2008 | Broome et al. |
| 7,780,635 | B2 * | 8/2010 | Pruitt et al. ............. 604/187 |
| 2003/0093915 | A1 * | 5/2003 | Pearl et al. |
| 2005/0251242 | A1 * | 11/2005 | Bousfield et al. |

OTHER PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Yu et al., 2006, American Journal of Pathology, vol. 168, No. 6, p. 1879-1888.*
Cotsarelis, G., 2006, The Journal of Clinical Investigation, vol. 116, No. 1, p. 19-22.*

* cited by examiner

*Primary Examiner* — Shin-Lin Chen
(74) *Attorney, Agent, or Firm* — Wood, Herron & Evans, LLP

(57) ABSTRACT

A method of restoring hair to skin that has suffered hair loss includes optically ablating an array of spaced-apart microchannels or voids into the skin and transplanting into the voids stem cells, a scaffold and a differentiation factor for causing the stem cells to differentiate into hair follicles.

19 Claims, 11 Drawing Sheets

TREATMENT OF ALOPECIA BY MICROPORE DELIVERY OF STEM CELLS

CROSS-REFERENCE TO RELATED APPLICATIONS

This application claims benefit of and priority under 35 U.S.C. §119(e) to U.S. Provisional Patent Application Ser. No. 60/911,796, "Treatment of Alopecia by Micropore Delivery of Stem Cells," by inventors Basil M. Hantash, George Frangineas, and Leonard C. DeBenedictis, filed Apr. 13, 2007, which is incorporated herein by reference in its entirety.

TECHNICAL FIELD OF THE INVENTION

The present invention relates in general to methods of hair restoration. The invention relates in particular to growing hair from stem cells implanted in tissue in which hair loss has taken place.

INTRODUCTION

Alopecia, or hair loss, is a common problem in men and women worldwide. Currently, only a few treatment options exist. These are topical rogaine (minoxidil) and oral propecia (finasteride). Neither treatment is particularly effective and propecia is only approved for use in men. Alopecia has a significant impact on quality of life, mainly by causing emotional trauma and diminishing self-esteem. Recently, a light-based application has been developed for the treatment of alopecia; however, this therapy has been disappointing to date.

The standard of care is hair transplantation surgery. This treatment involves removal of a band of hair from the posterior scalp followed by hair follicle isolation and subsequent implantation into pre-cored posterior implantation sites over the region of interest. A problem with this process is that it is quite tedious, as only between about 500 to about 800 hairs may be transplanted in a half-day session. This represents merely a nominal amount of hair when considering the fact that a full scalp bears close to one-million hairs. Furthermore, hair transplantation is limited by the availability of remaining hair on the patient's scalp. Accordingly, this procedure is best performed earlier in the natural history of the disease, a time when patients may not be prepared to undergo such an extensive surgical intervention. Because of this, a lot of patients choose to undergo artificial hair transplantation, but this procedure, although simpler to perform, leads to unnatural aesthetic appearance. A method of promoting hair growth non-invasively is therefore desirable.

One possible method would be to introduce stem cells capable of differentiating into a hair follicle phenotype in order to promote hair growth on human skin. Stem cells have recently received a significant amount of attention due to their potential to regenerate tissue and organs. For example, stem cells isolated from the hair bulge region of the follicle explanted into nude mouse skin have given rise to hair follicles and sebaceous glands in animal models. To date, no method has been developed in order to utilize stem cells in humans to grow hair and treat problems such as alopecia.

One problem with using hair-bulge stem cells is the difficulty of isolating this rare cell from the donor. Although methods exist for expanding the stem cell in vitro, each passage of stem cells during tissue culture diminishes the odds that multipotential differentiation is preserved. Furthermore, specifically for the hair-bulge stem cell, expansion may not be feasible, as much of the current scientific experimentation suggests that hair-bulge stem cells lose their ability to differentiate into hair follicles after the first passage. In addition, to avoid issues of immune-dependent rejection, the recipient must also serve as the donor.

Another problem lies in finding an effective method of implanting the stem cells. Such a method must be relatively painless and preferably capable of being implemented over relatively large areas, for example, one-hundred square centimeters ($cm^2$) or more. Previous scientific experiments on animals have involved an instrument-dependent, "cookie-cutter" approach of mechanically perforating or cutting skin to provide channels for receiving the stem cells. Problems of pain and wound healing notwithstanding, such an approach is almost as tedious and time consuming as the above discussed hair-transplanting. Absent a solution to these problems, implementation of such a method in humans may remain quite difficult and even impossible to commercialize.

SUMMARY OF THE INVENTION

The present invention is directed to compositions and methods of restoring hair to skin that has suffered hair loss. In one aspect, the inventive methods include irradiating the skin with laser radiation in a manner such that a plurality of elongated spaced-apart voids are formed in the skin. The voids extend into the dermis of the skin. Stem cells and at least one hair follicle differentiation factor are implanted into the voids for promoting hair growth in the skin.

In one aspect of the invention, laser ablation forming the spaced-apart voids causes the voids to be surrounded with coagulated tissue immediately following the irradiation. There is viable tissue remaining between the voids. The coagulated tissue is under tension resulting from collagen shrinkage by heat generated during the abrasion process. The tension in the coagulated tissue shrinks the voids. The stem cells, a scaffold, and the differentiation factor or factors are deposited into the voids. A healing process completely replaces the coagulated tissue with new tissue after a period of about one month.

In another aspect, the present invention provides an apparatus for treating or preventing hair loss in a subject in need thereof, the apparatus comprises a handpiece movable over skin wherein the handpiece is arranged to receive an optical beam and focus the optical beam at a plurality of spaced-apart locations on the skin thereby creating a plurality of voids in the skin for the deposition of a composition, wherein the composition comprises a stem cell and a growth media.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

DETAILED DESCRIPTION OF THE INVENTION

Figure 1:
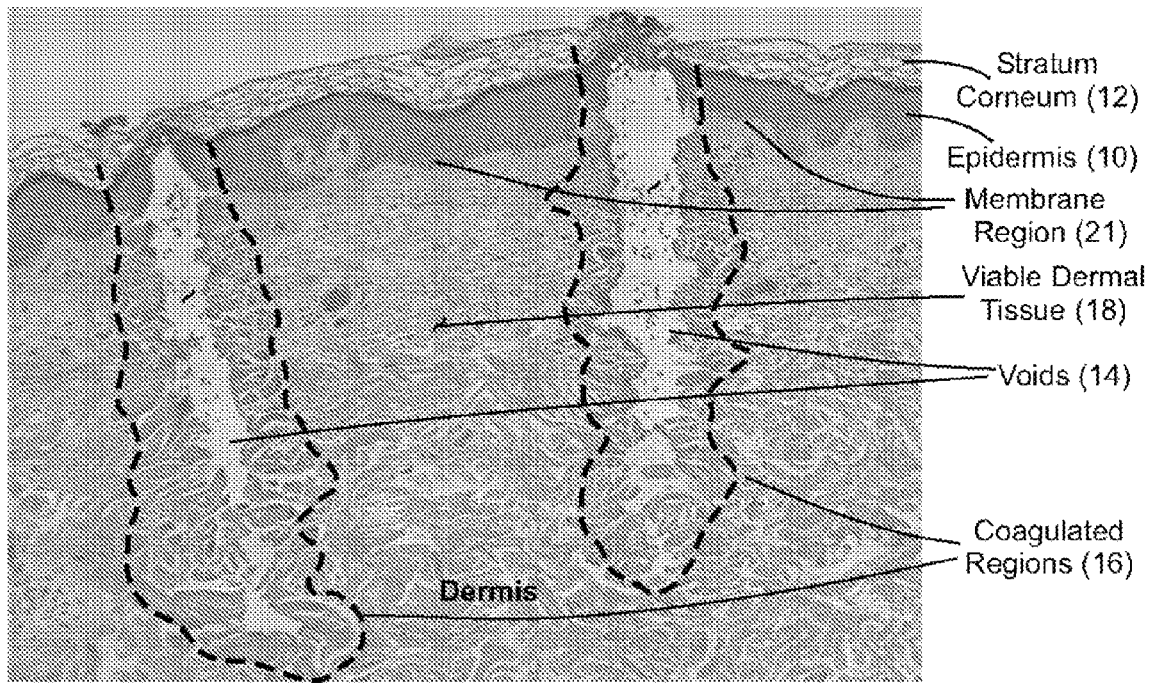
FIG. 1 is a micrograph of a section of human skin immediately after irradiation with laser radiation having parameters in accordance with the method of the present invention, the irradiated skin including a plurality of voids extending through the stratum corneum and the epidermis into the dermis, the voids being surrounded by regions of coagulated dermal tissue with viable tissue between the regions of coagulated tissue surrounding the voids.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. The practice of the present invention will employ, unless otherwise indicated, conventional methods of preparative and analytical methods of chromatography, protein chemistry, biochemistry, recombinant DNA techniques and pharmacology, within the skill of the art.

The present invention provides compositions and methods for the prevention and/or treatment of alopecia in a subject. The compositions of the invention comprise stem cells and a differentiation factor. The stem cells can be embryonic stem cells, fetal stem cells, umbilical cord stem cells, or adult stem cells. The differentiation factor can be one or more selected from the group consisting of nerve growth factor (NGF), platelet-derived growth factors (PDGF), thryootropin releasing hormone (TRH), transforming growth factor betas (TG-Fβs), insulin-like growth factor (IGF-1), and the like. The compositions can optionally comprise a scaffold. The methods of the invention comprise implanting compositions comprising stem cells, a scaffold, and a differentiation factor in human skin to promote hair growth. In one aspect, the compositions are implanted into one or more micropore channel (s) or void(s) in the skin, wherein the micropore channel(s) or void(s) can be created using laser irradiation of the skin. The micropore channel or void preferably extends through the stratum corneum and the epidermis into the dermis and is surrounded by regions of coagulated dermal tissue. Preferably viable tissue is present between adjacent micropore channels or voids. The viable tissue promotes healing of the treatment zones.

Thus, in one aspect of the invention, compositions comprising one or more stem cells, a differentiation factor, and optionally a scaffold, where the stem cell can be embryonic, fetal, umbilical cord blood, or adult derived. Stem cells useful for generating hair cells can be derived from a mammal, such as a human, mouse, rat, pig, sheep, goat, or non-human primate. Stem cells are unspecialized cells capable of extensive proliferation. Stem cells are pluripotent and are believed to have the capacity to differentiate into most cell types in the body, including neural cells, muscle cells, blood cells, epithelial cells, skin cells, and hair cells. Further, stem cells are capable of ongoing proliferation in vitro without differentiating. As they divide, they retain a normal karyotype, and they retain the capacity to differentiate to produce adult cell types.

The present invention encompasses compositions and methods for treating or preventing hair loss in a subject. Aspects according to the invention include methods for delivering stem cells, preferably adult stem cells, derived from, for example, the hair follicle bulge and dermal papilla, epidermal layer of skin, adipose tissue, bone marrow, or peripheral blood of an individual, to the area of the subject in need of therapy. Alternatively, the stem cells can be from embryonic stem cells isolated from the inner cell mass of preimplantation embryos. Stem cells can also be derived from umbilical cord blood or from fetal tissue. Also included are methods for the delivery of the stem cells. The stem cells (derived from adult, fetal, umbilical cord blood or embryonic sources) to be delivered can be derived from the skeletal muscle, adipose tissue, bone marrow, or other tissue samples, or the cells may be cultured, expanded, combined or manipulated before delivery. One cell type or a combination of cell types can also be delivered. In addition, the cells may be delivered along with a natural or synthetic cellular scaffolding material and/or carrier solution, and with or without bioactive agents.

Cells suitable for implantation in the present invention include stem cells from embryonic, fetal, umbilical cord blood and adult stem cells. Typically, these differentiate to form different types of cells, or, they can be converted to a wide variety of immunologically neutral cells that have been programmed to function as undifferentiated pluripotent cells. The cells can be genetically engineered or nonengineered, and mixtures of such cells also can be used. The stem cell can be modified such that it is surface antigen negative for CD44, CD45, and HLA Class I and II. The stem cell can also be surface antigen negative for CD34, Muc18, Stro-1, HLA-class-I and can be positive for oct3/4 mRNA, and hTRT mRNA. In particular, the stem cell can be surface antigen negative for CD31, CD34, CD36, CD38, CD45, CD50, CD62E and CD62P, HLA-DR, Muc18, STRO-1, cKit, Tie/Tek, CD44, HLA-class 1 and 2-microglobulin and is positive for CD10, CD13, CD49b, CD49e, CDw90, Flk1, EGF-R, TGF-R1 and TGF-R2, BMP-R1A, PDGF-R1 and the like. The stem cells with modified surface antigens can be useful for modulating the immunological response, such as, for example, reducing the immunogenicity of the transplanted cells.

Typically, the tissue is harvested from, for example, adipose tissue, bone marrow, blood or other tissues where adult stem cells may be found, fetal tissue, umbilical cord blood, or embryos where embryonic stem cells are found. Further, stem cells can be obtained from donor tissue, such as donor skin or scalp, by dissociation of individual cells from the connecting extracellular matrix of the tissue. Tissue can be removed using a sterile procedure, and the cells can be dissociated using any method known in the art including treatment with enzymes such as trypsin, collagenase, and the like, or by using physical methods of dissociation such as with a blunt instrument. For example, adipose tissue is readily accessible and abundant in most individuals and can be harvested by liposuction. Various liposuction techniques exist, including ultrasonic-assisted liposuction ("UAL"), laser-assisted liposuction, and traditional suction-assisted liposuction ("SAL"), where fat is removed with the assistance of a vacuum created by either a mechanical source or a syringe. Each of the foregoing liposuction techniques can be used in conjunction with tumescent solution. Liposuction procedures that use a tumescent solution generally involve pre-operative infiltration of subcutaneous adipose tissue with large volumes of dilute anesthetic solutions. Adipose may also be harvested during panniculectomy or abdominoplasty procedures.

Another advantage of using adipose tissue as a source of adult stem cells is that, due to the abundance of stem cells in adipose tissue, stem cell harvest, isolation, genetic manipulation and/or growth-factor based differentiation may be accomplished peri-operatively. Thus, depending on the number of cells required for implantation, it may not be necessary for the patient to submit to the liposuction procedure on one day and the stem cell implantation on a subsequent day. The procedures can be performed sequentially within minutes or tens of minutes of one another.

In another aspect, the stem cells can be hair follicle stem cells and melanocyte stem cells isolated from tissue of an adult mammal, preferably a human. The cells include but are not limited to, melanocyte stem cells responsible for producing melanocytes that put pigment into the hair shaft and the multi-potent hair follicle stem cell that gives rise to different epidermal structures, e.g. the hair shaft, sebaceous glands, sweat glands, and epidermal keratinocytes. Different hair follicle stem cells can be isolated from other cells by means known in the art. Melanocytes can be readily identified from other cells. For example, melanocytes contain microphthalmia transcription factor. Although the multi-potent stem cell that gives rise to the hair shaft, sebaceous glands, sweat glands, and epidermal keratinocytes is exemplified herein, the methods of ex vivo propagation described herein can be applied to any hair follicle stem cell whether it be muti-potent, pluripotent, or a unique progenitor subtype, such as a stem cell that produces only sebaceous glands and not, for example, sweat glands.

The somatic hair follicle stem cells act as precursor cells, which produce daughter cells that mature into differentiated hair follicle cells. The hair follicle stem cells can be isolated from the individual in need of hair follicle stem cell therapy, or from another individual. Somatic hair follicle stem cells may be immune-privileged, so the graft versus host disease after allogenic transplant may be minimal or non-existent. Hair follicle stem cells can be administered by any known means, for example, intravenous injection, or injection directly into the appropriate tissue, such as the skin on the scalp. For example, intact hair follicles can be dissected from the skin under sterile conditions. The hair shaft can then be resected at its point of exit from the follicle. The intact follicle can be digested with enzymes, repeatedly washed, and filtered with a nylon mesh to remove external cells (e.g., dermal fibroblasts) that adhere to the follicle capsule. The follicle can be opened with a single longitudinal incision and placed in culture medium.

Alternatively, bone marrow may be harvested for adult stem cells. Bone marrow is a complex tissue comprised of two distinct populations of stem cells, namely hematopoietic stem cells and mesenchymal stem cells. Hematopoietic stem cells give rise to components of the blood and immune systems while mesenchymal stem cells give rise to varied cells, including osteoblasts, chondrocytes, adipocytes, fibroblasts, smooth muscle cells, and myoblasts. Cells, such as fibroblasts, reticulocytes, adipocytes and endothelial cells, form a connective tissue network called "stroma." Cells from the stroma regulate morphologically the differentiation of hematopoietic cells through direct interaction via cell surface proteins and the secretion of growth factors.

In yet another embodiment, adult stem cells may be derived from peripheral blood. Human blood has circulating adult progenitor cells that can be capable of differentiating into hair cells in response to platelet derived growth factor (PDGF-BB) treatment. Thus, in one aspect of the present invention, a blood draw is contemplated. Since progenitor cell populations are present in blood in very low percentages, the cells are expanded in culture following growth factor-induced differentiation and selection. Alternatively, the patients may be systemically treated with agents, such as granulocyte-colony stimulating factor (G-CSF), granulocyte monocyte colony-stimulating factor (GM-CSF), or the like.

In a next step, stem cells can be isolated from the harvested tissue. In general, methods of isolation of cells includes not only harvesting a tissue specimen, but also processing the specimen so that the cells contained therein are substantially dissociated into single cells rather than grouped as cell clusters. Dissociating the cells into single cell components can be accomplished by any method known in the art; e.g., by mechanical (filtering) or enzymatic means. Further, the isolating step includes combining the cell-containing specimen with a cell culture medium comprising factors that stimulate cell growth without differentiation. Next, the specimen-medium mixture is cultured for a few up to many cell passages.

Appropriate culture medium is described in the art. For example, stem cells can be cultured in serum free DMEM/high-glucose and F12 media (mixed 1:1), and supplemented with N2 and B27 solutions and growth factors. Growth factors such as EGF, IGF-1, and bFGF have been demonstrated to augment sphere formation in culture. In vitro, stem cells often show a distinct proliferation potential for forming spheres. Thus, the identification and isolation of spheres can aid in the process of isolating stem cells from mature tissue for use in making differentiated hair cells. The growth medium for cultured stem cells can contain one or more or any combination of growth factors, provided that the stem cells do not differentiate. To induce the cells (and the cells of the spheres) to differentiate, the medium can be exchanged for medium lacking growth factors. For example, the medium can be serum-free DMEM/high glucose and F12 media (mixed 1:1) supplemented with N2 and B27 solutions. Equivalent alternative media and nutrients can also be used. Culture conditions can be optimized using methods known in the art.

The culture medium can be supplemented with a proliferation-inducing growth factor(s). As used herein, the term "growth factor" refers to a protein, peptide or other molecule having a growth, proliferative, differentiative, or trophic effect on stem cell. Growth factors that can be used include any trophic factor that allows hair follicle stem cells to proliferate, including any molecule that binds to a receptor on the surface of the cell to exert a trophic, or growth-inducing effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGFα), and combinations thereof. Growth factors can be added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor.

Hair follicle stem cells can be cultured in suspension or on a fixed substrate. For example, the stem cells can be grown on a hydrogel, such as a peptide hydrogel, as described below. Alternatively, the stem cells can be propagated on tissue culture plates or in suspension cultures. Cell suspensions can be seeded in any receptacle capable of sustaining cells, particularly culture flasks, cultures plates, or roller bottles, more particularly in small culture flasks such as 25 cm$^2$ cultures flasks. Preferably, the hair follicle stem cells are grown on tissue culture plates, and can be cultured at high cell density to promote the suppression of asymmetric cell kinetics.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C. Cells are preferably cultured for 3-30 days, preferably at least about 7 days, more preferably at least 10 days, still more preferably at least about 14 days. Cells can be cultured substantially longer. They can also be frozen using known methods such as cryopreservation, and thawed and used as needed.

Another preferred embodiment provides for deriving clonal lines of somatic hair follicle stem cells by limiting dilution plating or single cell sorting. Methods for deriving clonal cell lines are well known in the art.

Protocols for the identification of cells that differentiate into hair cells are known. The cells can be monitored for expression of cell-specific markers. For example, hair cells can be identified by the expression of myoVIIa, Math1, α9 acetylcholine receptor, espin, parvalbumin 3, or Brn3.1. Selection can be accomplished by fluorescence activated cell sorting (FACS), magnetic activated cell sorting (MACS), western blotting, or by other techniques known by those skilled in the art.

The changes that induce a stem cell to differentiate, such as into a hair cell, involve altered biochemical pathways that lead to a specific phenotype. These alterations are a result of the expression of specific genes, and this expression pattern can be influenced by signals from the environment of the cell including cell-cell contact, oxygen content, nutrient availability, ligands that bind to receptors on the cells, temperature, and other factors.

Proteins that influence (e.g., promote or inhibit differentiation) the phenotype of hair cells include developmental regulators, cell cycle inhibitors, transcription factors and other regulatory proteins that act on stem cells. The phenotype of the cell includes the characteristics that distinguish it from other cell types. For example, the phenotype of a hair cell is distinct from the phenotype of a spiral ganglion cell.

Agents capable of causing stem cells to differentiate are referred to as differentiation agents. Differentiation agents can be, for example, small molecules, antibodies, peptides (e.g., peptide aptamers), antisense RNAs, small inhibitory RNAs (siRNA), or ribozymes. Differentiation agents, such as small molecules, can modulate the activity of one or more of the proteins that influence cell phenotype by altering the activity of a growth factor or receptor, an enzyme, a transcription factor, or a cell-specific inhibitor. These molecules can change the binding affinity of a protein for another protein, or can bind in an active site of an enzyme or act as an agonist or antagonist of a ligand binding to a receptor. Some types of differentiation agents, such as small inhibitory RNAs (siRNAs), antisense RNAs, or ribozymes, can modify the expression pattern of genes that encode these proteins. Furthermore, the agents can be useful as therapeutic agents for treating hearing disorders or vestibular dysfunction.

A differentiation agent can cause a stem cell to differentiate, at least partially, into a hair cell. The differentiation agent can be a polypeptide, such as an aptamer or antibody; a nucleic acid, such as DNA or RNA; or a compound, such as a small molecule. For example, an agent is contacted with a stem cell, and the stem cell is determined to differentiate, at least partially, into a hair cell. The differentiation agent can be naturally occurring or synthetic, and can be obtained from a library, or identified by other methods.

A variety of methods can be utilized to determine that a stem cell has differentiated at least partially into a hair cell. For example, the cell can be examined for the expression of a cell marker gene. Hair cell marker genes include myosin VIIa (myoVIIa), Math1, α9 acetylcholine receptor, espin, parvalbumin 3, and Brn3.1. A pluripotent stem cell does not express these genes. A stem cell that propagates and produces a cell expressing one or more of these genes, has produced a hair cell, i.e., the stem cell has differentiated at least partially into a hair cell. A stem cell that has differentiated into a progenitor cell (a precursor of hair cells) expresses early marker genes such as Sox1, Nestin, Pax2, Bmp7, Jagged1, or $p27_{Kip1}$. A progenitor cell can express one or more of these genes. The progenitor cells can be propagated in serum-free medium in the presence of growth factors. Removal of growth factors will induce the cells to differentiate further, such as into hair cells.

Identification of a hair cell or hair cell progenitor (e.g., a hair cell or progenitor cell that differentiated from a stem cell) can be facilitated by the detection of expression of tissue-specific genes. Detection of gene expression can be by immunocytochemistry. Immunocytochemistry techniques involve the staining of cells or tissues using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for calorimetric reactions, or gold beads (for electron microscopy), or with the biotin-avidin system, so that the location of the primary antibody, and thus the antigen, can be recognized. The protein marker can also be detected by flow cytometry using antibodies against these antigens, or by Western blot analysis of cell extracts.

Tissue-specific gene expression can also be assayed by detection of RNA transcribed from the gene. RNA detection methods include reverse transcription coupled to polymerase chain reaction (RT-PCR), Northern blot analysis, and RNAse protection assays.

In some embodiments, a differentiation agent can be tested against stem cells that have been engineered to express a reporter gene that facilitates detection of cells converted into inner ear cells. These engineered stem cells make up a reporter cell line. A reporter gene is any gene whose expression may be assayed; such genes include, without limitation, green fluorescent protein (GFP), α-glucuronidase (GUS), luciferase, chloramphenicol transacetylase (CAT), horseradish peroxidase (HRP), alkaline phosphatase, acetylcholinesterase and β-galactosidase. Other optional fluorescent reporter genes include but are not limited to red fluorescent protein (RFP), cyan fluorescent protein (CFP) and blue fluorescent protein (BFP), or any paired combination thereof, provided the paired proteins fluoresce at distinguishable wavelengths.

A reporter gene can be under control of a promoter that is active in hair cells, including progenitor cells and cells at varying degrees of differentiation, but not in stem cells. Ideally, the promoter is stably upregulated in the differentiated cells or progenitors cells to allow assessment of the partially or fully differentiated phenotype (e.g., expression of the reporter gene and further identification of genes known to be expressed in the hair cell). In one exemplary embodiment, the luciferase gene is the reporter gene, which is under control of a promoter active in hair cells, such as a myoVIIa promoter. Since myoVIIa is primarily expressed in hair cells and in only a few other cell types, the partial or full conversion of the stem cells to hair cells will result in increased luminescent signal, whereas conversion of stem cells to most other cell types will not increase luciferase expression.

The stem cells described above, such as the expanded hair follicle stem cells, can be used for a variety of purposes, including, but not limited to, hair transplant therapy, such as transplantation of hair follicles or skin grafts containing transplanted stem cells into the scalp or skin. One can administer the hair follicle stem cells and optionally melanocyte stem cells to individuals desiring treatment for or prevention of hair loss in the same manner conventional hair transplants use. Hair follicle stem cells are particularly useful for treating or preventing hair loss, such as caused by male pattern baldness or alopecia. As such, hair loss is combated by the ability of the stem cells, such as the hair follicle stem cells, to produce hair. For example, transplantation of hair follicle stem cells into the scalp can increase the number of functional hair follicles in balding individuals. Such transplantation could complement or replace follicular unit transplantation (FIT), the current means of hair restoration.

The method of transplantation involves the preparation of recipient site with a laser that creates microscopic recipient wells approximately 50-250 microns in diameter, as described in detail below. The recipient site can be prepared by introduction of a commercially available scaffold such as but not limited to poly(lactic-co-glycolic acid) (PLGA), fibronectin, collagen 1, or collagen 3. The scaffold material can include a self-assembling molecule, such as, for example, a peptide hydrogel, a carbon nanotube, and mixtures thereof. The scaffold can be introduced after laser injury but prior to cell transplantation. Individual hair follicles, where hair follicle stem cells have been introduced can be transplanted, by applying a stem cell impregnated biogel dressing onto the laser injured recipient site. The recipient site covered by the cellular dressing would then be sealed using petrolatum and tegaderm or another biological dressing.

Implanted hair follicle stem cells (constituted by hair bulge stem cells, dermal papilla stem cells, and/or keratinocytes used in isolation or in combinations ranging from 0-100% each) are differentiated in vivo by steps using serum free medias supplemented with inductive growth factors.

The first step is the induction of the hair follicle placode. After stem cells have successfully been grafted into the laser recipient site through the use of a scaffold and appropriate dressing as described above, the stem cells are then treated with a serum free media containing FGF2, FGF4, or noggin at concentrations known in the art (1-100 ng/ml). Each growth factor can be used individually or in combination. Noggin is known to block the activity of BMP2, BMP4, and FGF5—all cytokines that are inhibitory to hair follicle morphogenesis during this early stage of development. FGF2 and FGF4 induce the expression of Sonic hedgehog (SHH) which is a powerful morphogen and inducer of the hair follicle placode.

After the hair follicle bud has sprouted within the base of the cavitary lesion created by the laser injury of scalp or skin, stem cells continue to proliferate over the following 1 to 21 days leading to the development of hair follicle germ and finally a hair follicle peg. In the ensuing weeks, a bulbous peg can be generated through the continued exposure to FGF2 or FGF4 or Noggin.

The media can then be replaced with serum free media containing either PDGF or PTHrp, or combinations of the two (1-100 ng/ml), in order to further induce downgrowth of the bulbous peg and subsequent formation of the dermal papilla.

Finally, anagen can be initiated by the replacement of the media with a serum free media containing FGF7 (1-100 ng/ml). This allows the hair to begin to grow and cycle similar to a normal hair.

Figure 2:
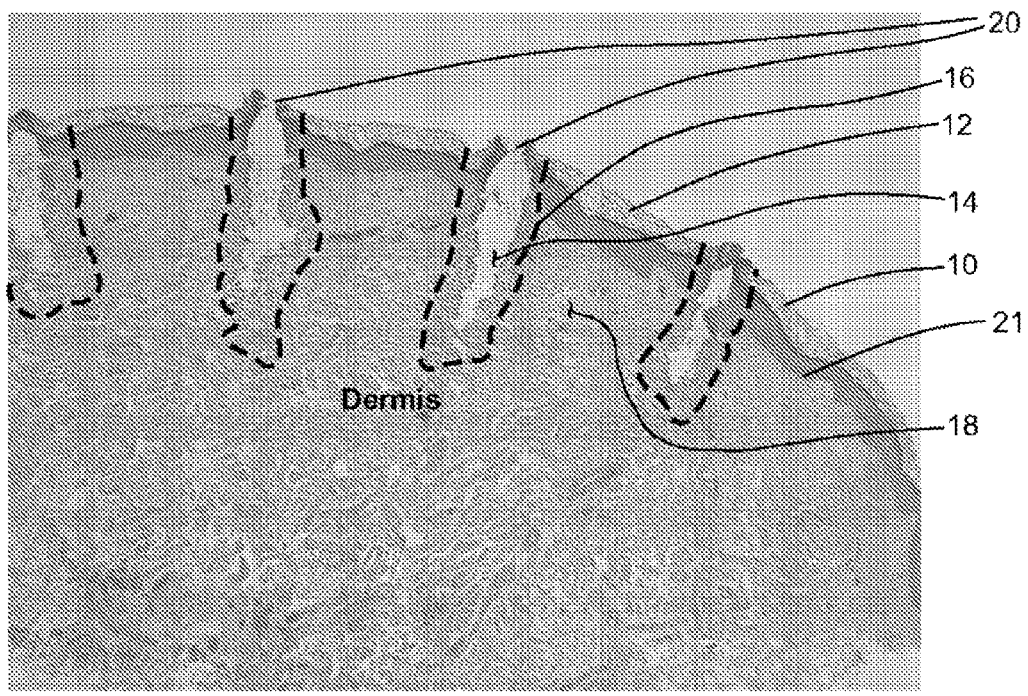
FIG. 2 is a micrograph similar to the micrograph of FIG. 1 but having a lower magnification and depicting detail of the voids extending through the stratum corneum.

Referring now to the drawings, wherein like features are designated by like reference numerals, FIG. 1 and FIG. 2 are micrographs schematically illustrating a section of human skin immediately after immediately after irradiation with laser radiation to provide microchannels or voids capable of receiving stem cells in accordance with the method of the present invention. FIG. 2 is at twice the magnification of FIG. 1. The skin was irradiated at spaced-apart locations with pulses of radiation having a wavelength of 10.6 micrometers (μm) from a $CO_2$ laser delivering a substantially $TEM_{00}$-quality beam. Each location was irradiated by one pulse. The radiation at the locations was focused to a spot having a diameter of about 120 μm at the surface of the skin, expanding slightly to between about 150 μm and 170 μm at a depth of about 1 mm in the skin. The laser output was repetitively pulsed at a pulse repetition frequency (PRF) of about 60-100 Hz. The pulses were nominally "square" laser pulses having a peak power of about 40 Watts (W) and a pulse duration of about 0.5 milliseconds (ms) to produce a pulse energy of 20 millijoules (mJ). The pulse duration could be varied to create different pulse energies for other experimental treatments. Experimental evaluations were performed with pulse energies in a range between about 5 mJ and 40 mJ. Laser pulses were scanned over the surface using a scanner wheel device to provide the spaced apart voids. The PRF of the laser was synchronized with the rotation of the scanner wheel. A detailed description of a preferred example of such a scanner wheel is presented further hereinbelow.

The skin tissue includes a bulk dermal portion or dermis covered by an epidermal layer (epidermis) 12 typically having a thickness between about 30 μm and 150 μm. The top layer of the epidermis is covered, in turn, by a stratum corneum layer 10 typically having a thickness between about 5 μm and 15 μm. Tissue was ablated at each pulse location, producing a plurality of spaced-apart voids 14, elongated in the direction of incident radiation, and extending through the stratum corneum and the epidermis into the dermis.

In the example of FIGS. 1 and 2, the voids with the parameters mentioned above have an average diameter (width) of between about 180 μm and 240 μm. These dimensions are provided merely for guidance, as it will be evident from the micrographs that the diameter of any one void varies as the result of several factors including, for example, the inhomogeneous structure and absorption properties of the tissue. The voids have an average depth of between about 800 µm and 1000 µm, and are distributed with a density of approximately 400 voids per square centimeter ($cm^2$). Walls of the voids are substantially cauterized by heat generated due to the ablation, thereby minimizing bleeding in and from the voids. This heat also produces a region 16 of coagulated tissue (coagulum) surrounding each void. Note that the term "surrounding" as used in this application does not imply that there is tissue remaining above the void. Here, the void is defined as being surrounded by coagulated tissue if dermal tissue around the walls of the void is coagulated. The void is defined as the region that is ablated. Immediately following ablation the voids are open. The appearance of closure of some voids in FIG. 2 is believed to be an artifact of the preparation of tissue samples for microscopic evaluation.

The coagulated regions have a thickness between about 20 µm and 80 µm immediately after ablation of the voids. Here again, however, thickness varies randomly with depth of the void because of above-mentioned factors affecting the diameter of the void. Between each void 14 and the surrounding coagulum 16 is a region of 18 of viable tissue. This includes a viable region of the stratum corneum, the epidermis, and the dermis. Preferably the region of viable tissue has a width, at a narrowest point thereof, at least about equal to the maximum thickness of the coagulated regions 16 to allow sufficient space for the passage of nutrients to cause rapid healing and to preserve an adequate supply of transit amplifying cells to perform the reepithelialization of the wounded area. More preferably, the viable tissue separating the coagulated tissue around the voids has a width, at a narrowest point thereof, between about 50 µm and 500 µm. A preferred density of treatment zones is between about 200 and 4000 treatment zones per $cm^2$. The density of treatment zones can be higher than the desired hair density because not every stem cell implantation sites will produce a viable hair follicle. This treatment-zone density can be achieved in a single pass or multiple passes of a treatment device of applicator, for example two to ten passes, in order to minimize gaps and patterning that may be present if treatment zones are created in a single pass of the applicator.

Heat from the ablation process that causes the coagulation in regions 16 effectively raises the temperature of the collagen in those coagulated regions sufficiently to create dramatic shrinkage or shortening of collagen in the coagulated tissue. This provides a hoop of contractile tissue around the void at each level of depth of the void. Upon collagen shrinkage, the dermal tissue is pulled inward, effectively tightening the dermal tissue. This tightening pulls taut any overlying laxity through a stretching of the epidermis and stratum corneum. This latter response is primarily due to the connection of a basement membrane region 21 of the epidermis to the collagen and elastin extra-cellular matrix. This connection provides a link between the epidermis and dermis. The contractile tissue very quickly shrinks the void, and creates an increase in skin tension resulting in a prompt significant reduction in overall skin laxity and the appearance of wrinkles. This shrinkage mechanism is supplemented by a wound-healing process healing described below.

The micropore channels or pores created as described above are used to deposit a composition comprising a stem cell and a growth media in order to promote the stem cell to regenerate a hair in the location of the micropore channels or voids. The micropore channels or voids can extend through the stratum corneum and the epidermis into the basal layer of the epidermis and are surrounded by regions of coagulated tissue. The micropore channels or voids can extend through the epidermis into the dermal-epidermal junction and are surrounded by regions of coagulated tissue. The micropore channels or voids can extend through the epidermis into the dermis and are surrounded by regions of coagulated tissue. In one example, the micropore channels or voids can be created using an electromagnetic radiation treatment that is delivered in a fractional manner, leaving viable tissue present between adjacent micropore channels or voids. The viable tissue remaining between the micropore channels and voids helps promote healing of the micropore channels or voids. Additionally, ablative electromagnetic radiation treatments delivered in a fractional manner can be optimized so as to produce voids of similar depth and similar or larger diameter as naturally occurring hair follicles. Using $CO_2$ laser treatments delivered in a fractional manner has been found to produce such voids.

The process of producing micropore channels or voids using electromagnetic energy delivered in a fractional manner can be used to create a follicular regenerative environment in the skin. The creation of a follicular regenerative environment in the skin by producing the voids using electromagnetic energy induces the surrounding untreated tissue to migrate into the void.

The creation of a follicular regenerative environment in the skin by producing voids also stimulates one or more hair regenerative signals within the tissue. The hair regenerative signal can comprise a growth factor, a cytokine, and the like. The hair regenerative signal induces invagination of hair regeneration competent epidermal stem cells into the void. The hair regenerative signal initiates a cascade of regenerative signals with temporal equivalence to the hair regeneration signals of embryological skin found at the outset of hair development.

The hair regenerative signal can mimic the embryological hair induction signal. By mimicking the embryological hair induction signal, the hair regenerative signal can promote the induction of hair regeneration upon introduction of an exogenous stem cell. The hair regenerative signal can promote the proper orientation and polarity of an induced hair follicle. By promoting the proper orientation and polarity of an induced hair follicle, the hair regenerative signal can reduce the likelihood that the treatment will result in the formation of an epidermal cyst.

The hair regeneration signal and/or the invagination of epidermal stem cells into the void can promote the attachment, development and/or proliferation of an exogenous stem cells placed into the void. The exogenous stem cell can be a hair follicle stem cell from an autologous source. The exogenous stem cell can be a hair follicle stem cell from an allogeneic source. The hair follicle stem cell can be an epidermal stem cell, a dermal papilla stem cell, a stem cell that is mesenchymal in origin, a stem cell that is embryonic in origin, a stem cell that is ectodermal in origin, or a combination thereof.

The hair regenerative signal can persist for a period of time sufficient to promote permanent hair follicle cycling, such as, for example, for about 1 to about 6 months. The hair regenerative signal can promote the permanent hair follicle cycling.

Closure of the void occurs within a period of about 48 hours or less through a combination of the above-described prompt collagen shrinkage and the subsequent wound healing response. The wound healing process begins with re-epithelialization of the perimeter of the void, which typically takes less than 24 hours, formation of a fluid filled vacuole, followed by infiltration by macrophages and subsequent dermal remodeling by the collagen and elastin forming fibroblasts. The column of coagulated tissue has excellent mechanical integrity that supports a progressive remodeling process without significant loss of the original shrinkage. In addition, the coagulated tissue acts as a tightened tissue scaffold with increased resistance to stretching. This further facilitates wound healing and skin tightening. The tightened scaffold serves as the structure upon which new collagen is deposited during wound healing and helps to create a significantly tighter and longer lasting result than would be created without the removal of tissue and the shrinkage due to collagen coagulation.

Figure 3:
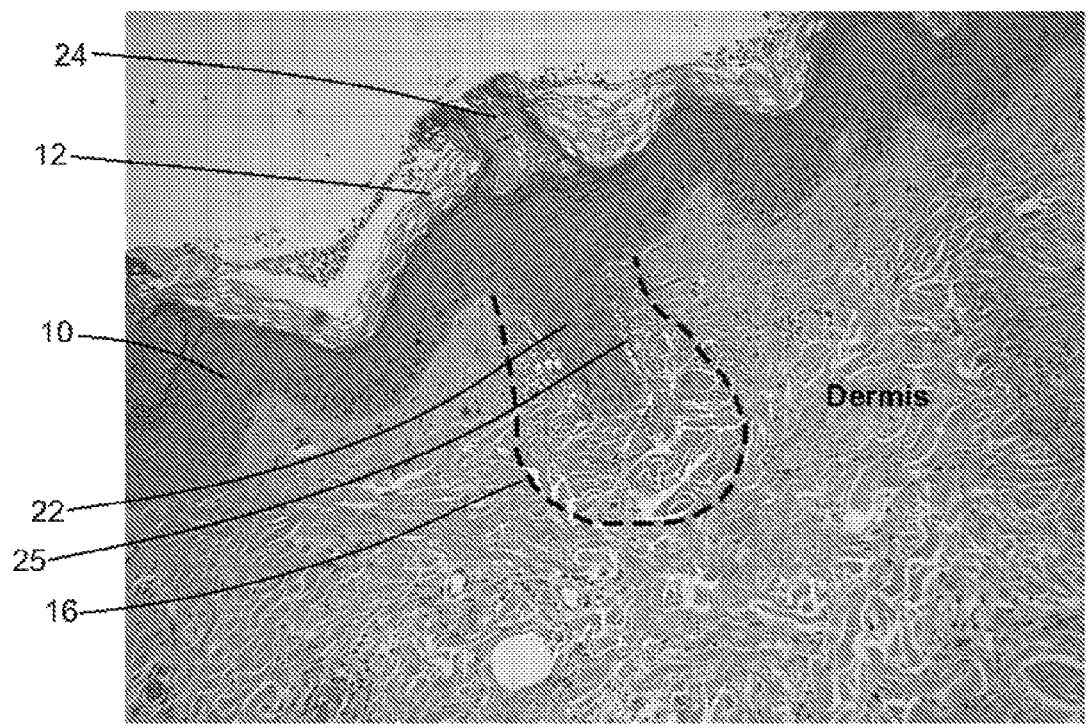
FIG. 3 is a micrograph of a section of human skin 48 hours after irradiation with laser radiation in having the parameters in accordance with the method of FIG. 1.

Progress of the healing after a period of about 48 hours from the irradiation conditions of FIG. 1 is illustrated by the micrograph of FIG. 3, which has the same magnification. Here, the coagulated region 16 is reduced both in diameter and depth compared with a comparable region of FIG. 1. In the micrograph of FIG. 3 epidermal stem cells have migrated into the void and facilitated healing of the void area. Epidermal stem cells proliferate and differentiate into epidermal keratinocytes filling the void in a centripetal fashion. As epidermal cells proliferate and fill the void, the coagulated material is pushed up the epidermis toward the stratum corneum. The voids contain microscopic-epidermal necrotic debris (MEND). The pushing of the coagulated material forces a plug 24 of the MEND to seal the stratum corneum during the healing response, thus preventing access of the outside environment to the inside of the skin.

At this time, the basement membrane is ill-defined and has yet to be completely repaired and restored. This is clearly depicted by the vacuolar space 25 separating the healed void and the dermis. In FIGS. 1 and 2, there is sparse cellularity evident in the dermis. However, in the micrograph of FIG. 3, the wound healing response at 48 hours has led to increased release of signaling molecules, such as chemokines, from the area of spared tissue, leading to recruitment of inflammatory cells aiding in the healing response.

Figure 4:
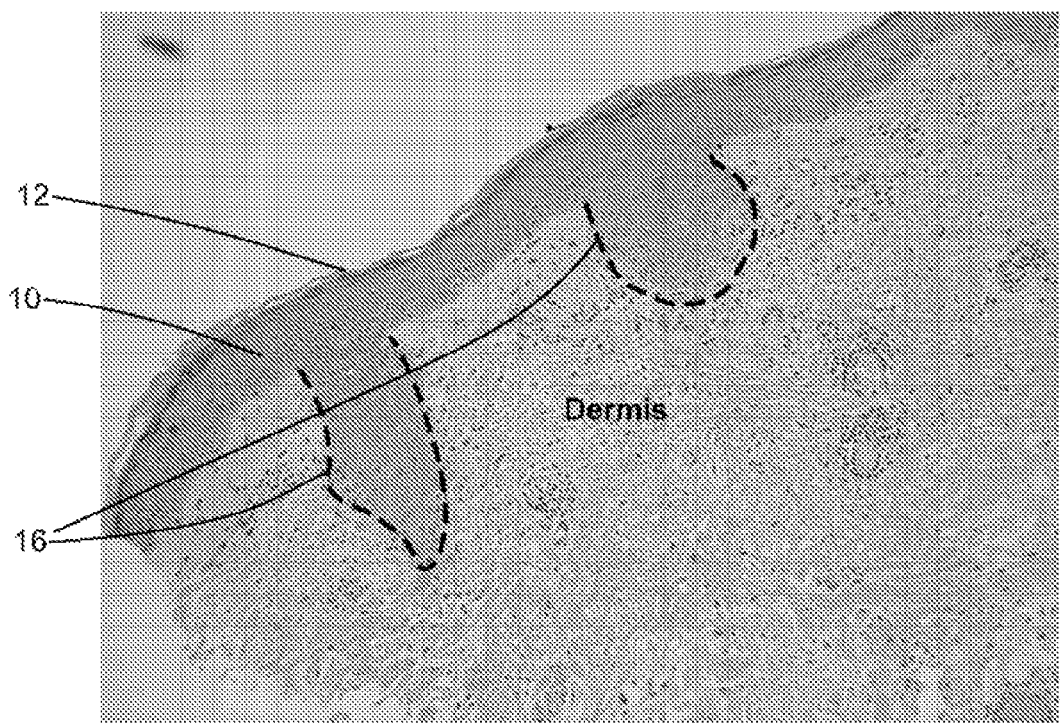
FIG. 4 is a micrograph of a section of human skin one week after irradiation with laser radiation in having the parameters in accordance with the method of FIG. 1.

Progress of the healing after a period of about one week from the irradiation conditions of FIG. 1 is illustrated by the micrograph of FIG. 4. Here, the MEND has been exfoliated. The void has been replaced by epidermal cells which gradually remodel to create a normal rete ridge pattern, reducing in depth of invagination. The healing process has triggered that some of the deeper epidermal cells go through apoptosis, thereby disappearing from the replaced void tissue. The basement membrane of the epidermis has almost fully been restored as evidenced by the lack of vacuolization between the epidermis and dermis. During the wound healing response, cytokines such as TGF beta, amongst others, are released and allow fibroblasts to secrete collagen, elastin, and extracellular matrix. This secreted matrix replaces the apoptotic epidermal cells of the void. The coagulated dermal tissue has been replaced by a similar process sparked by the laser irradiation treatment induced release of pro-neocollagenesis cytokines. Inflammatory cells also help remove non-viable debris in the dermis, allowing the replacement of coagulated tissue with fresh viable tissue as outlined above.

Figure 5:
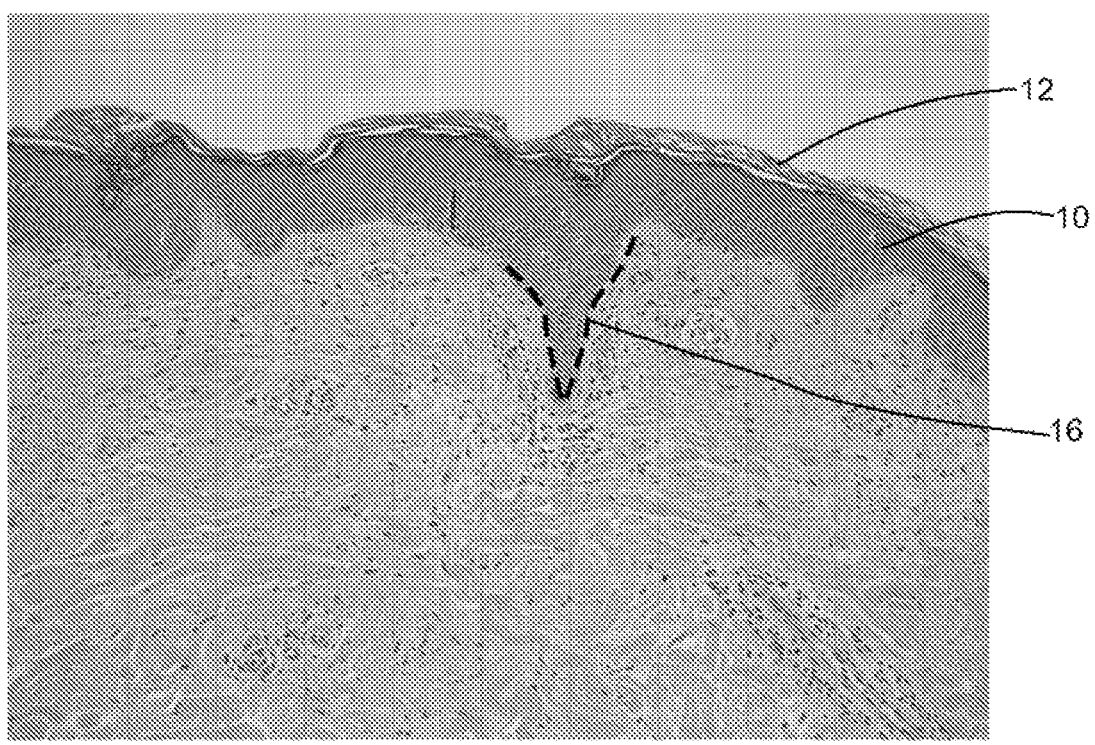
FIG. 5 is a micrograph of a section of human skin one month after irradiation with laser radiation in having the parameters in accordance with the method of FIG. 1.

FIG. 5 depicts progress of healing one month after initial treatment. Here remodeling of the void has continued by apoptosis of the deeper epidermal cells, leading to a more natural rete ridge like structure. The MEND is absent, and the basement membrane of the epidermis is completely healed. Inflammatory cells are still present in the dermis, and fibroblasts continue to lay down new matrix in the dermis. This provides that over the ensuing two to six months, new collagen synthesis continues to replace previously coagulated dermal tissue, providing for increased tensile strength in the dermis.

The complete replacement of the coagulated tissue providing the initial skin tightening with new collagen and elastin as described above provides for a long lasting improvement in the appearance of wrinkles in temporally or photo aged skin. As the inventive method results in a completely healthy treated area once the healing process is complete, an area of skin treated once can be treated again, for example, after a period of about two months to provide further improvement. Clearly, however, the progress of skin aging and loosening can not be arrested permanently, and the length of time that any improved appearance will be evident will depend on the age of the person receiving the treatment and the environment to which treated skin is exposed, among other factors.

In the example described above, skin irradiation for void formation is performed with laser radiation having a wavelength (10.6 µs) that is strongly absorbed by water. Preferably the radiation is delivered as a beam having $TEM_{00}$ quality, or near $TEM_{00}$ quality. The $CO_2$ laser used in the example of the present invention discussed above is a relatively simple and relatively inexpensive laser for providing such a beam. The 10.6 µm radiation of a $CO_2$ laser has an absorption coefficient in water of approximately 850 inverse centimeters ($cm^{-1}$). To efficiently ablate tissue, a high absorption coefficient in the water of the skin tissue is desired. However, in order to form a coagulation region surrounding the voids, to cause tissue shrinkage and to reduce bleeding at the treatment sites, the absorption coefficient should not be too high. Preferably, laser radiation used in the inventive method should have an absorption coefficient in water in the range between about 100 $cm^{-1}$ and 12,300 $cm^{-1}$. More preferably, the absorption coefficient should be between about 100 $cm^{-1}$ and 1000 $cm^{-1}$ and more preferably in the range between about 500 $cm^{-1}$ and 1000 $cm^{-1}$. In each of these absorption levels, laser pulses for forming the voids preferably have a duration between about 100 microseconds (µs) and 5 ms. The actual treatment parameters can be chosen based on commercial tradeoffs of available laser powers and desired treatment-zone sizes. Lasers providing radiation having a wavelength that has an absorption coefficient in water in the preferred ranges include $CO_2$, CO, and free-electron lasers (500-1000 $cm^{-1}$), thulium-doped fiber lasers and free-electron lasers (100-1000 $cm^{-1}$), Er:YAG lasers, raman-shifted erbium-doped fiber lasers, and free-electron lasers (between about 100 $cm^{-1}$ and 12,300 $cm^{-1}$). Other light sources, such as optical parametric oscillators (OPOs) and laser pumped optical parametric amplifiers (OPAs) can also be used.

Voids 14 preferably have a diameter between about 100 µm and 500 µm, and are preferably spaced apart with a center to center distance of between about 200 µm and 1500 µm depending on the size of the voids 14 and the coagulated regions 16. The center to center distance can be chosen based on the level of desired treatment. A coverage area for the coagulated regions and voids immediately following treatment is preferably between about 5% and 50% of the treated area. A higher level of coverage will be more likely to have a higher level of side effects for a similar treatment energy per treatment site. A preferred depth of the voids is between about 200 µm and 4.0 millimeters (mm). The voids are preferably randomly distributed over an area of skin being treated.

In relative and practical terms, the voids are preferably placed such that coagulated zones 16 surrounding the voids are separated by at least the average thickness of the coagulated zones. This can be determined by making micrographs of test irradiations, similar to the above-discussed micrographs of FIGS. 1 and 2. If voids are too closely spaced, the healing process may be protracted or incomplete. If voids are spaced too far apart, more than one treatment may be necessary to achieve an acceptable improvement. Regarding depth of the voids, the voids and surrounding coagulated zones must extend into the dermis in order to provide significant skin tightening. The voids should preferably not, however, completely penetrate the skin or extend into subcutaneous fatty tissue.

Figure 6:
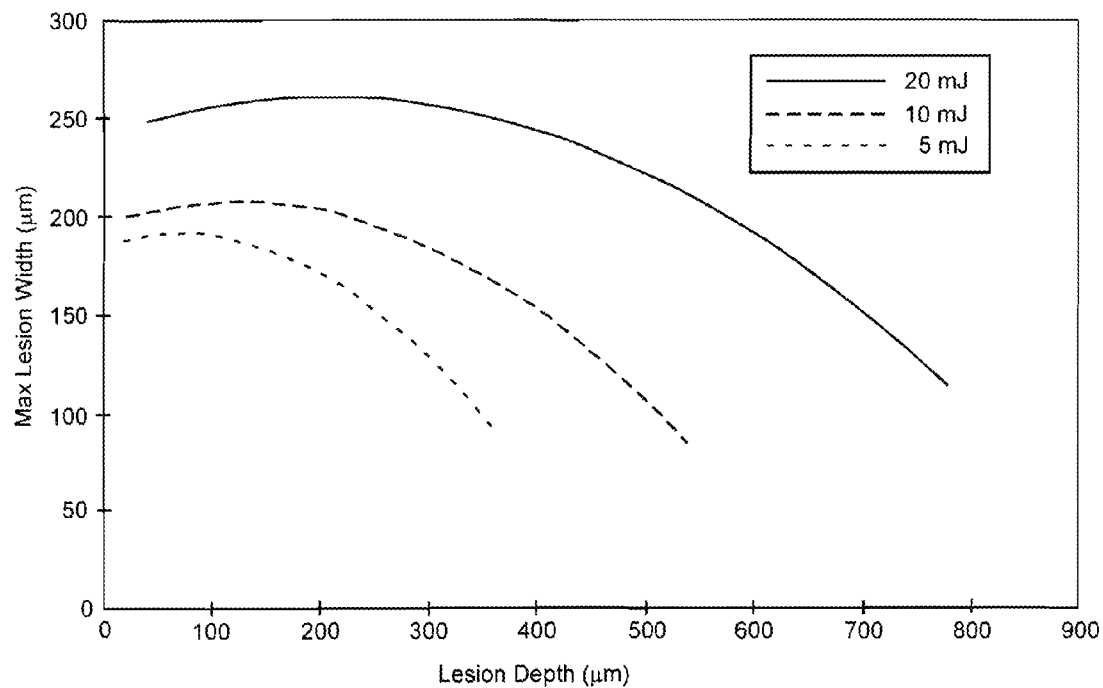
FIG. 6 is a graph schematically illustrating trend curves for maximum lesion or treatment zone with (void width plus coagulated tissue width) as a function of lesion or zone depth in the method of the present invention, for 5 mJ, 10 mJ, and 20 mJ pulses.
Figure 7:
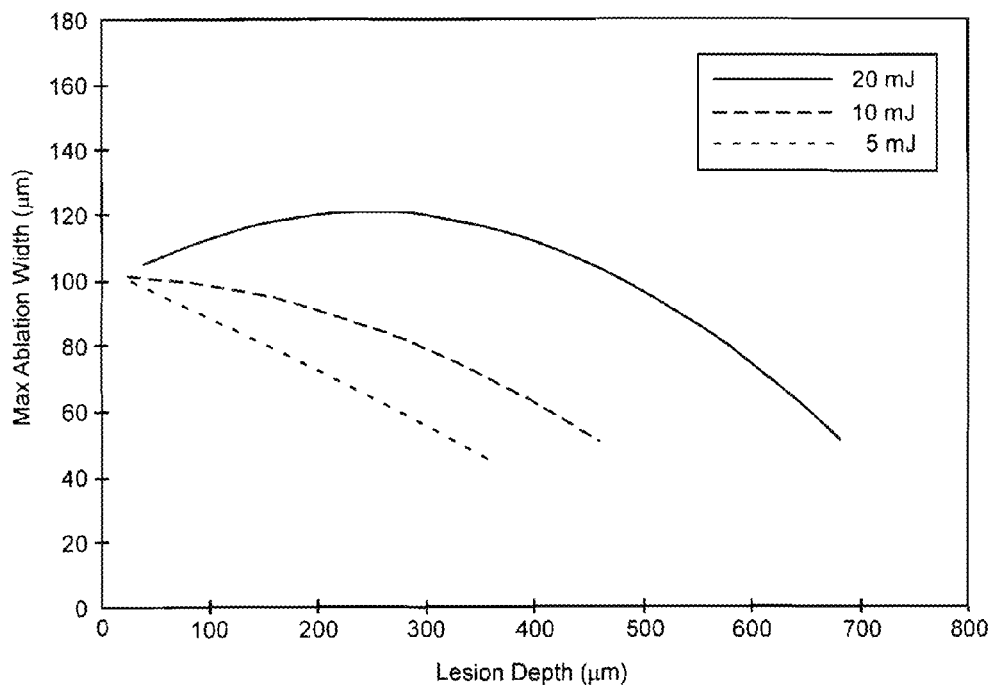
FIG. 7 is a graph schematically illustrating trend curves for maximum void width as a function of lesion or zone depth in the method of the present invention, for 5 mJ, 10 mJ, and 20 mJ pulses.

FIG. 6 and FIG. 7 are graphs schematically illustrating respectively trends for maximum width of the a treatment zone (lesion), i.e., maximum total width of a void 14 plus surrounding coagulated region 16, and maximum width of the void (ablated region), as a function of lesion depth, i.e., the depth to the base of the coagulated region. The trends in each graph are shown for pulse energies of 5 mJ, 10 mJ, and 20 mJ. It should be noted here that these trends fitted through a number of experimental measurements with relatively wide error bars, particularly at shallow lesion depth. Accordingly, it is recommended that these graphs be treated as guidelines only.

Figure 8C:
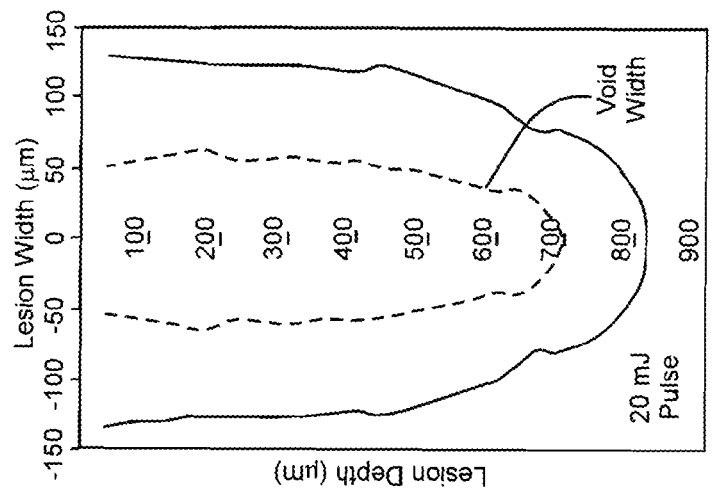
FIGS. 8A, 8B, and 8C are graphs schematically illustrating estimated width as a function of lesion or zone depth for lesions and voids with dimensions derived from micrographs of treatment sites in accordance with the present invention, for respectively 5 mJ, 10 mJ, and 20 mJ pulses.
Figure 8B:
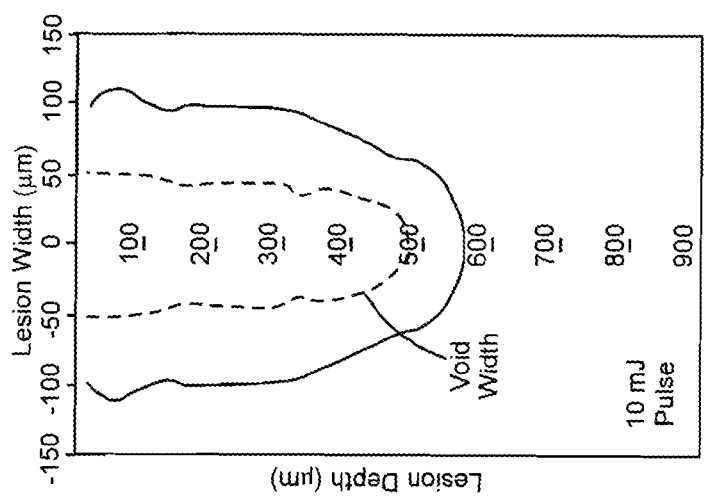
Figure 8A:
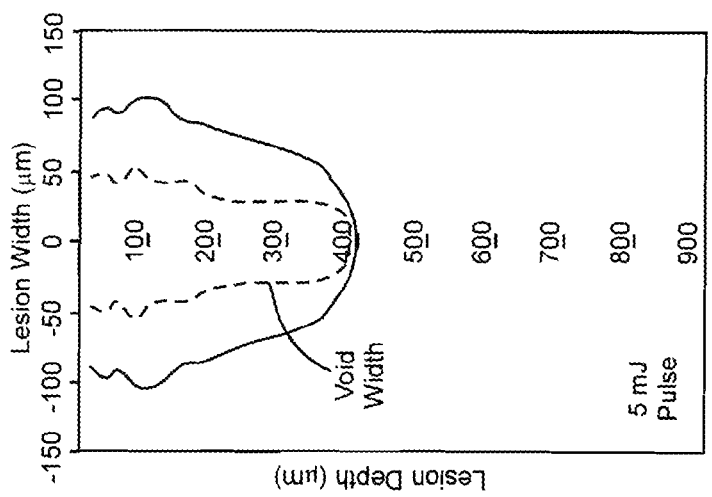

FIG. 8A, FIG. 8B, and FIG. 8C are graphs schematically illustrating graphical lesion width (solid curves) and void width (dashed curves) as a function of lesion depth for experimental irradiations at respectively 5 mJ, 10 mJ, and 20 mJ. These graphs are derived from measurements taken from micrographs of transverse sections through the experimental legions. The graphs of FIGS. 7 and 8A-C can be used as guidelines to select initial spacing of treatment zones in the inventive method. This spacing can then be optimized by experiment.

In any area being treated, ideally, all voids should be ablated simultaneously. However, apparatus capable of simultaneously ablating an effective number of voids with appropriate spacing over a useful area of skin may not be practical or cost effective. Practically, the voids can be ablated sequentially, but because of the rapid onset of the healing process, it is preferable that sequential ablation of tissue to create the voids in an area being treated is completed in a time period less than about 60 minutes (min). It is preferable to create voids at a rate between about 10 Hz and 5000 Hz and more preferably at a rate between about 100 Hz and 5000 Hz, because this rate reduces the physician time for treatment. Increasing the treatment rate above 5000 Hz causes the laser and scanning systems to be more expensive and therefore less commercially desirable, even though they are technologically feasible using the apparatus presented here. One preferred example of apparatus in accordance with the present invention for providing rapid sequential delivery of optical pulses and immediately thereafter introducing stem cells and differentiation factor into the voids is described below with reference to FIG. 9A, FIG. 9B, FIG. 9C, FIG. 10, and FIG. 11. FIGS. 9A-C and FIG. 10 depict apparatus for ablating the voids and FIG. 10 depicts an applicator including the void-ablating apparatus and means for introducing the stem cells and differentiation factor into the voids.

Figure 9A:
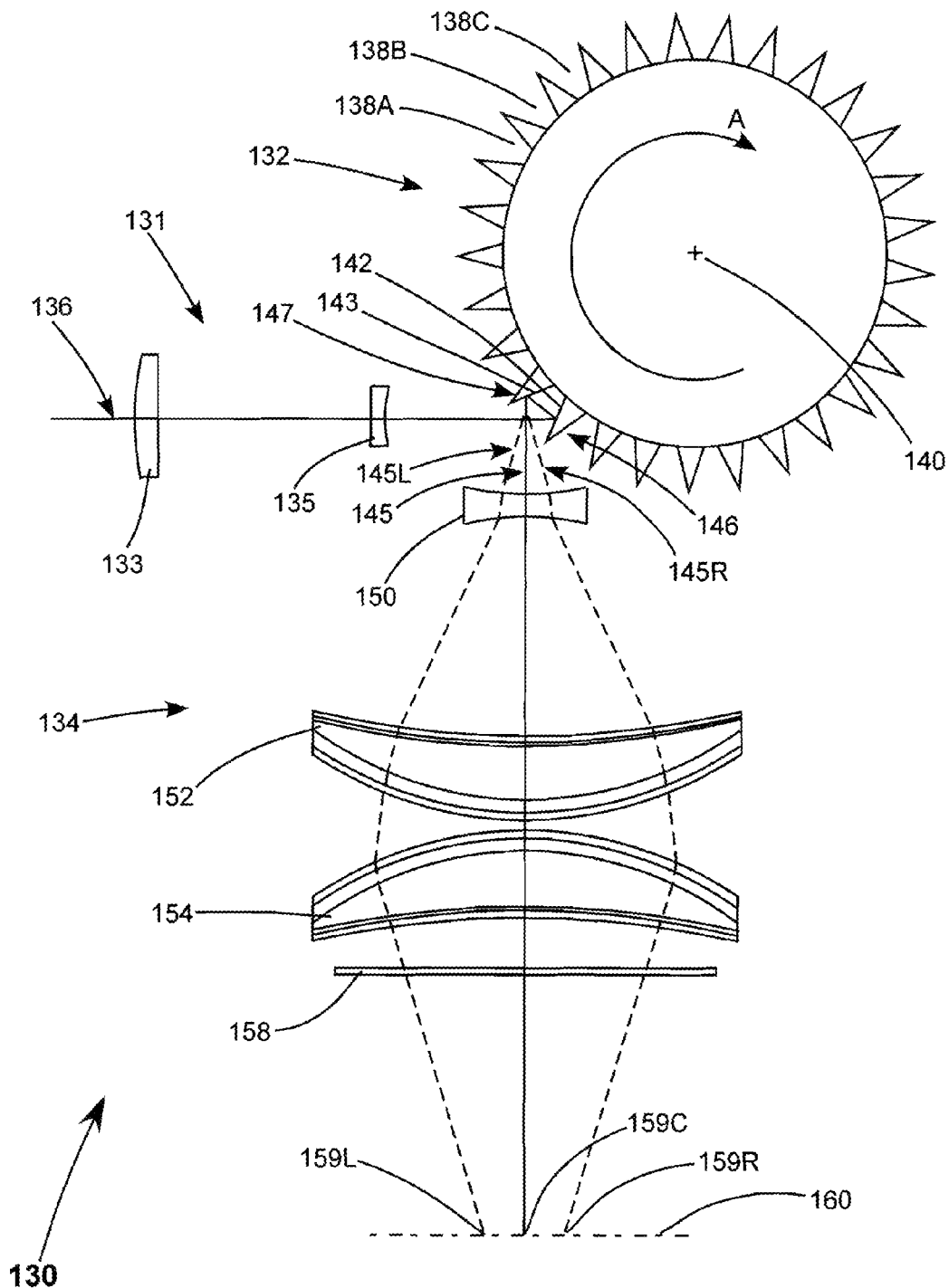
FIG. 9A is a front elevation view schematically illustrating one example of apparatus suitable for irradiating skin according to the method of the present invention, the apparatus including a multi-faceted scanning wheel for scanning a pulsed, collimated laser beam and a wide field lens for focusing the scanned laser beam onto skin to sequentially ablate tissue and create the cauterized voids of the inventive method.
Figure 9B:
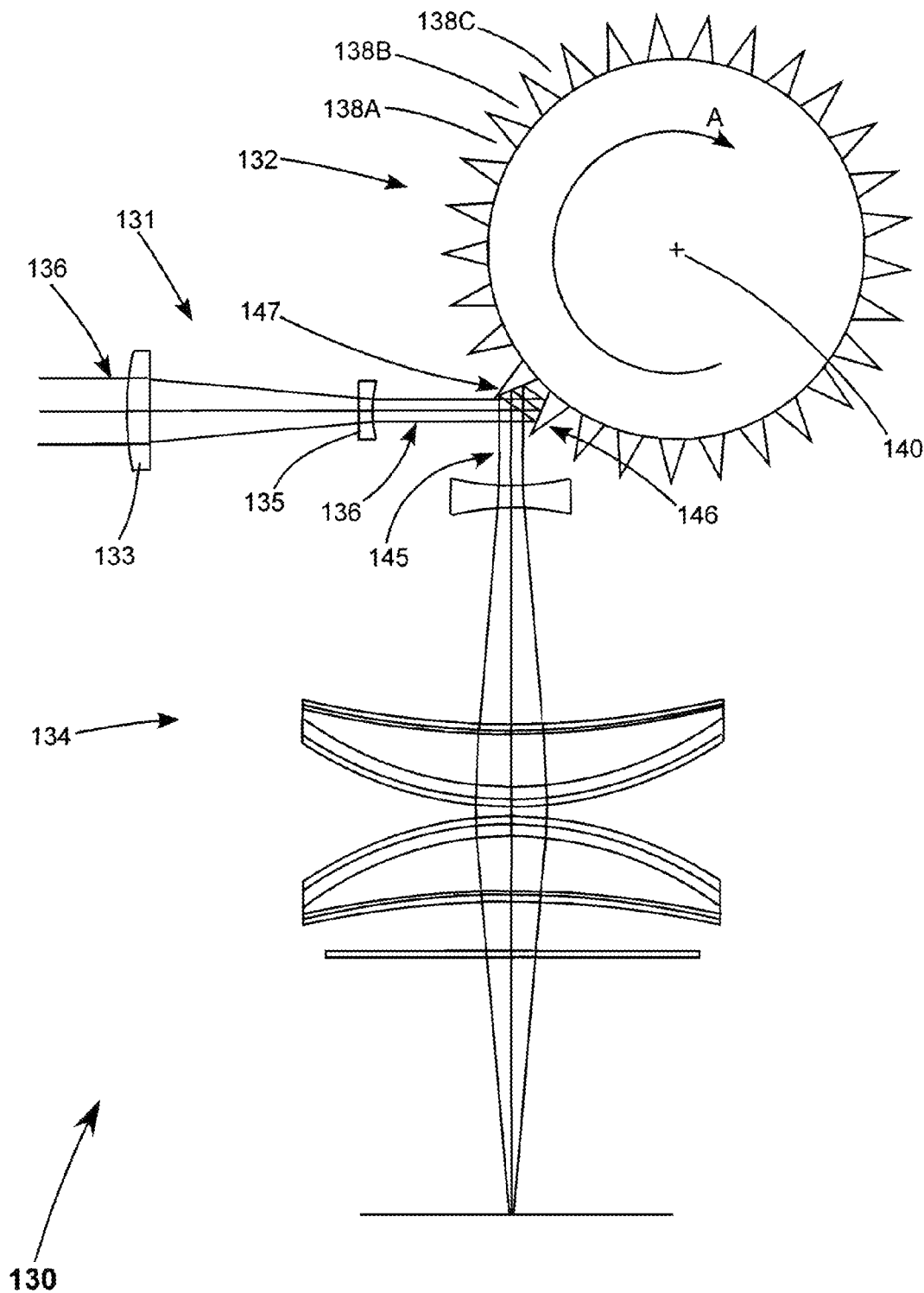
FIG. 9B is a front elevation view schematically illustrating further detail of beam focusing in the apparatus of FIG. 9A.
Figure 9C:
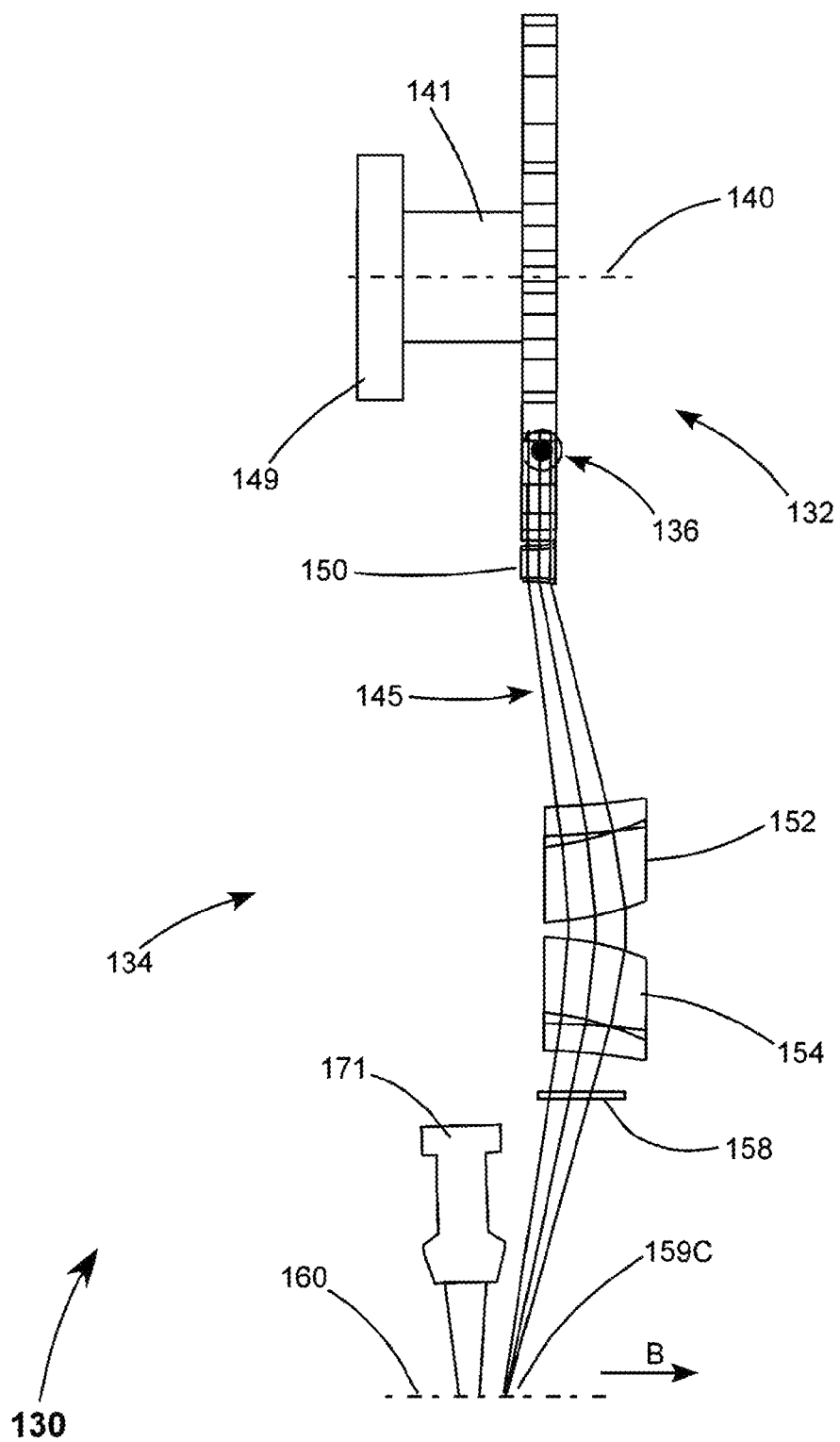
FIG. 9C is a side elevation view schematically illustrating still further detail of beam focusing in the apparatus of 9A.
Figure 10:
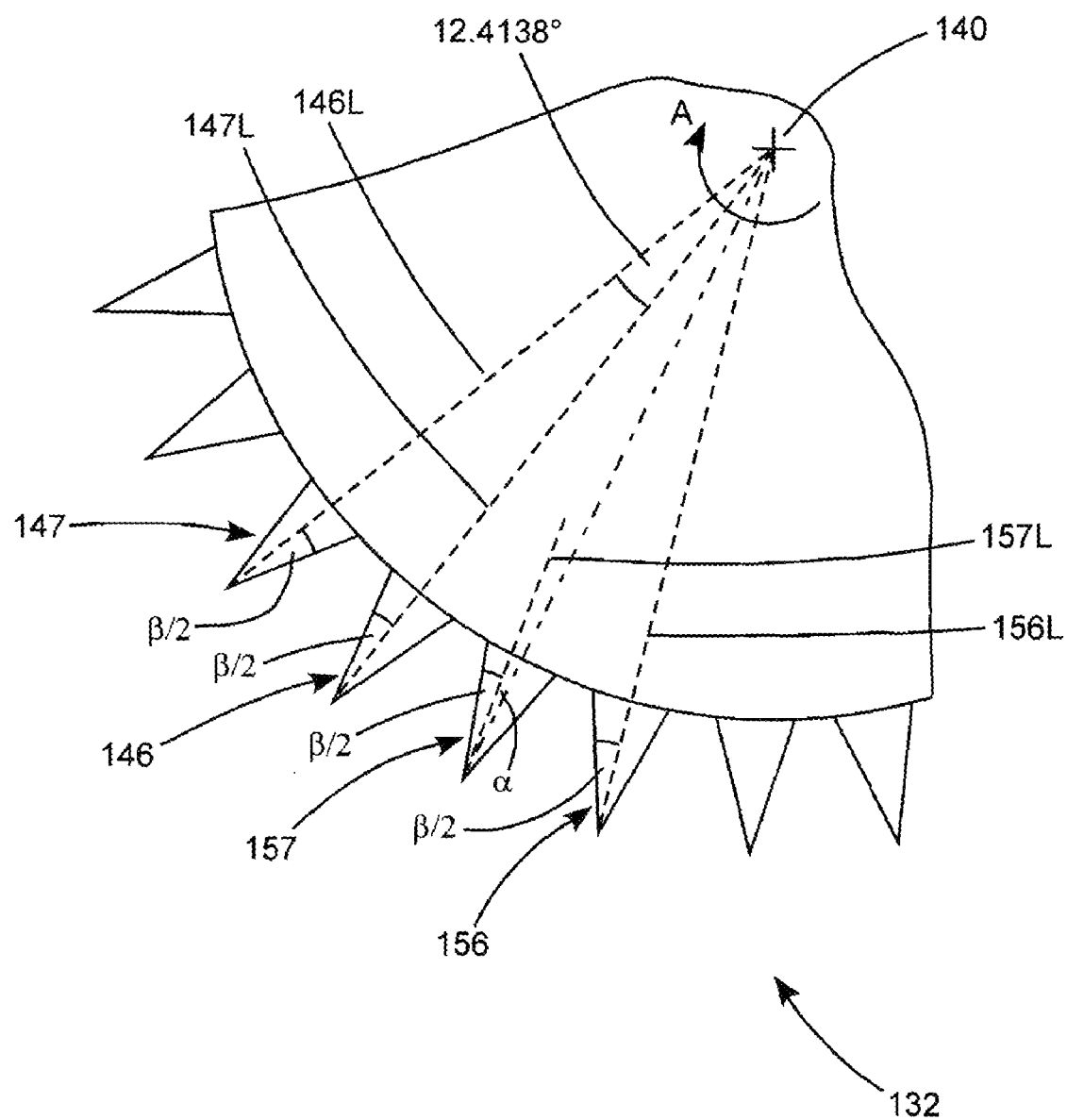
FIG. 10 schematically illustrates detail of the scanning wheel of FIGS. 9A-C.

Beginning with a description of the laser apparatus, FIG. 9A is a front elevation view schematically illustrating an ablation apparatus 130 including a scanner wheel 132 and a wide field projection lens 134. The scanner wheel is driven by a motor 149 via a hub 141 (see FIG. 9C). Scanner wheel 132 is arranged to receive an incident laser beam 136 lying substantially in the plane of rotation of the scanner wheel. In FIG. 9A beam 36 is represented by only a single principle ray. FIG. 9B and FIG. 9C are respectively front and side elevation views of apparatus in which beam 36 is represented by a plurality of rays.

Before being incident on the scanning wheel, beam 136 is compressed (see FIG. 9B) by a telescope 131 comprising a positive lens 133 and a negative lens 135. In this example, the scanner wheel divided into twenty nine sectors 138A, 138B, 138C, etc., which are arranged in a circle centered on the rotation axis 140 of the scanner wheel. The wheel, here, is assumed to rotate in a clockwise direction as indicated by arrow A. The incident laser beam 136 propagates along a direction that lies in the plane of rotation. Each sector 138 of scanner wheel 132 includes a pair of reflective elements, for example, reflective surfaces 142 and 143 for the sector that is indicated as being active. The surface normals of the reflective surfaces have a substantial component in the plane of rotation of the scanner wheel. In this example, the scanner wheel includes prisms 146, 147, etc. that are arranged in a circle. The faces of the prisms are reflectively coated and the reflectively coated surfaces of adjacent prisms, for example, reflective surfaces 142 and 143 from prisms 146 and 147, form the opposing reflective surfaces for a sector. Alternatively, the reflective surfaces can be metal surfaces that are polished to be smooth enough to cause sufficient reflectivity.

Each sector 138 deflects the incoming optical beam 136 by some angular amount. The sectors 138 are designed so that the angular deflection is approximately constant as each sector rotates through the incident optical beam 136, but the angular deflection varies from sector to sector. In more detail, the incident optical beam 136 reflects from the first reflective surface 132 on prism 146, and subsequently reflects from reflective surface 143 on prism 147 before exiting as output optical beam 145.

The two reflective surfaces 142 and 143 form a Penta mirror geometry. An even number of reflective surfaces that rotate together in the plane of the folded optical path has the property that the angular deflection of output beam 145 from input beam 136 is invariant with the rotation angle of the reflective surfaces. In this case, there are two reflective surfaces 142 and 143 and rotation of the scanner wheel 132 causes the prisms 146 and 147 and reflective surfaces 142 and 143 thereof to rotate together in the plane of the folded optical path. As a result, the output beam direction does not change as the two reflective surfaces 142 and 143 rotate through the incident optical beam 136. The beam can be focused at the treatment surface such that the beam does not walk across the surface during the scanning or the beam can be used at another plane such that the beam walks across the surface during the scanning due to the translation of the beam in a conjugate plane that translates into an angular variation during the scanning due to the rotation of the scanning wheel. The reflective surfaces 142 and 143 are self-compensating with respect to rotation of scanner wheel 32. Furthermore, as the reflective surfaces 142 and 143 are planar, they will also be substantially spatially invariant with respect to wobble of the scanner wheel.

As the scanner wheel rotates clockwise to the next sector 138 and the next two reflective surfaces, the angular deflection can be changed by using a different included angle between the opposing reflective surfaces. For this configuration, the beam will be deflected by an angle that is twice that of the included angle. By way of example, if the included angle for sector 138A is 45 degrees, sector 138A will deflect the incident laser beam by 90 degrees. If the included angle for sector 138B is 44.5 degrees, then the incident laser beam will be deflected by 89 degrees, and so on. In this example, different included angles are used for each of the sectors so that each sector will produce an output optical beam that is deflected by a different amount. However, the deflection angle will be substantially invariant within each sector due to the even number of reflective surfaces rotating together through the incident beam. For this example, the angular deflections have a nominal magnitude of 90 degrees and a variance of −15 to +15 degrees from the nominal magnitude. Beam 145 in extreme left and right scanning positions is indicated by dashed lines 45L and 45R respectively. Here again, in FIG. 9A beam 145 is represented by only a single principle ray, while FIG. 9B and FIG. 9B represent beam 145 by a plurality of rays.

Referring in particular to FIG. 10, in this example of scanner wheel 132, the apex angle of each prism is 32.5862 degrees, calculated as follows. Each sector 138 subtends an equal angular amount. Since there are twenty nine sectors, each sector subtends 360/29=12.4138 degrees. The two prisms 146 and 147 have the same shape and, therefore, the same apex angle $\beta$. Scanner wheel 132 is designed so that when the included angle is 45 degrees, the prisms 146 and 147 are positioned so that lines 147L and 146L that bisect the apex angle of prisms 146 and 147 also passes through the rotation axis 140. Accordingly, the design must satisfy an equation $\beta/2+12.4138+\beta/2=45$. Solving this equation yields an apex angle of $\beta=32.5862$ degrees.

The next prism 157 moving counterclockwise on scanner wheel 132 from prism 146 is tilted slightly by an angle $+\alpha$ so its bisecting line 157L does not pass through the center of rotation 140 of the scanner wheel. As a result, the included angle for the sector formed by prisms 146 and 157 is $(\beta/2+\alpha)+12.4138+\beta/2=45+\alpha$.

The next prism 156 is once again aligned with the rotation center 140 (as indicated by bisecting line 56L), so the included angle for the sector formed by prisms 56 and 57 is $(\beta/2-\alpha)+12.4138+\beta/2=45-\alpha$. The next prism is tilted by $+2\alpha$, followed by an aligned prism, and then a prism tilted by $+3\alpha$, followed by another aligned prism, etc. This geometry is maintained around the periphery of the scanner wheel. This specific arrangement produces twenty nine deflection angles that vary over the range of −15 degrees to +15 degrees relative to the nominal 90 degree magnitude. Note that this approach uses an odd number of sectors where every other (approximately) prism is aligned and the alternate prisms are tilted by angles $\alpha$, $2\alpha$, $3\alpha$, etc. In an alternate embodiment, the surface on which beam 136 is incident has zero tilt and all tilt is taken up in the reflective surface on the second facet.

Wide field lens 134, here includes optical elements 150, 152, and 154, and an output window 158. In the lens depicted in FIGS. 9A-C the optical elements are assumed to made from zinc selenide which has excellent transparency for 10.6-micrometer radiation. Those skilled in the art will recognize that other IR transparent materials such as zinc sulfide (ZnS) or germanium (Ge) may be used for elements in such a lens with appropriate reconfiguration of the elements. Optical elements 152, 154, and 156 are tilted off axis spherical elements. Lens 134 focuses exit beam 145 from scanner wheel 132 in a plane 160 in which skin to be treated would be located. Lens 134 focuses exit beam 145 at each angular position that the beam leaves scanner wheel 132. This provides a line or row sequence of 29 focal spots (one for each scanning sector of the scanner wheel) in plane 160. In FIG. 9A three of those spots are designated including an extreme left spot 159L, a center spot 159C and an extreme right spot 159R. The remaining 26 spots (not shown) are approximately evenly distributed between spots 159L, 159C, and 159R. Another line of focal spots can be produced by moving apparatus 130 perpendicular to the original line as indicated in FIG. 9C by arrow B.

Referring in particular to FIG. 9C, the tilted off-axis spherical elements 150, 152 and 154 are arranged such that beam 145 is first directed, (by bi-concave negative) lens element 150, away from the plane of rotation of the scanner wheel. Elements 152 and 154 (positive meniscus elements) then direct the beam back towards the plane or rotation, while focusing the beam, such that the focused beam is incident non-normally (non-orthogonally) in plane 160, i.e., normal to skin being treated. One particular of this non-normal incidence of beam 145 on the skin is that window 158 and optical element 154 are laterally displaced from the focal point and are removed from the principal path of debris that may be ejected from a site being irradiated. Another advantage is that a motion sensor optics for controlling firing of the laser in accordance with distance traveled by the apparatus, for example, an optical mouse or the like, designated in FIG. 9C by the reference numeral 171, may be directed close to the point of irradiation. This is advantageous for control accuracy. As far as he actual treatment is concerned, it is not believed that there is any advantage of non-orthogonal compared with non-orthogonal (normal incidence) irradiation.

Those skilled in the art will recognize that it is not necessary that all sectors of the scanner wheel have a different deflection angle. Prisms of the scanning wheel can be configured such that groups of two or more sectors provide the same deflection angle with the deflection angle being varied from group to group. Such a configuration can be used to provide less voids in a row with increased spacing therebetween. It is also not necessary that deflection angle be increased or decreased progressively from sector to sector. It is preferred in that pulsed operation of the laser providing beam 136, that the PRF of the laser is synchronized with rotation of the scanner wheel such that sequential sectors of the wheel enter the path of beam 136 to intercept sequential pulses from the laser.

It should be noted here that apparatus 130 including scanner wheel 132 and focusing lens 134 is one of several combinations of scanning and focusing devices that could be used for carrying out the method of the present invention and the description of this particular apparatus should not be construed as limiting the invention. By way of example, different rotary scanning devices and focusing lenses are described in U.S. patent application Ser. No. 11/158,907, filed Jun. 20, 2005, the complete disclosure of which is hereby incorporated by reference. Galvanometer-based reflective scanning systems can also be used to practice this invention and have the advantage of being robust and well-proven technology for laser delivery. Scanning rates with a galvanometer-based reflective scanning systems, however, will be more limited than with the a scanner such as scanning wheel 132 described above, due to the inertia of the reflective component and the changes of direction required to form a scanning pattern over a substantial treatment area. Other scanner systems can be used and are well known in the art.

Figure 11:
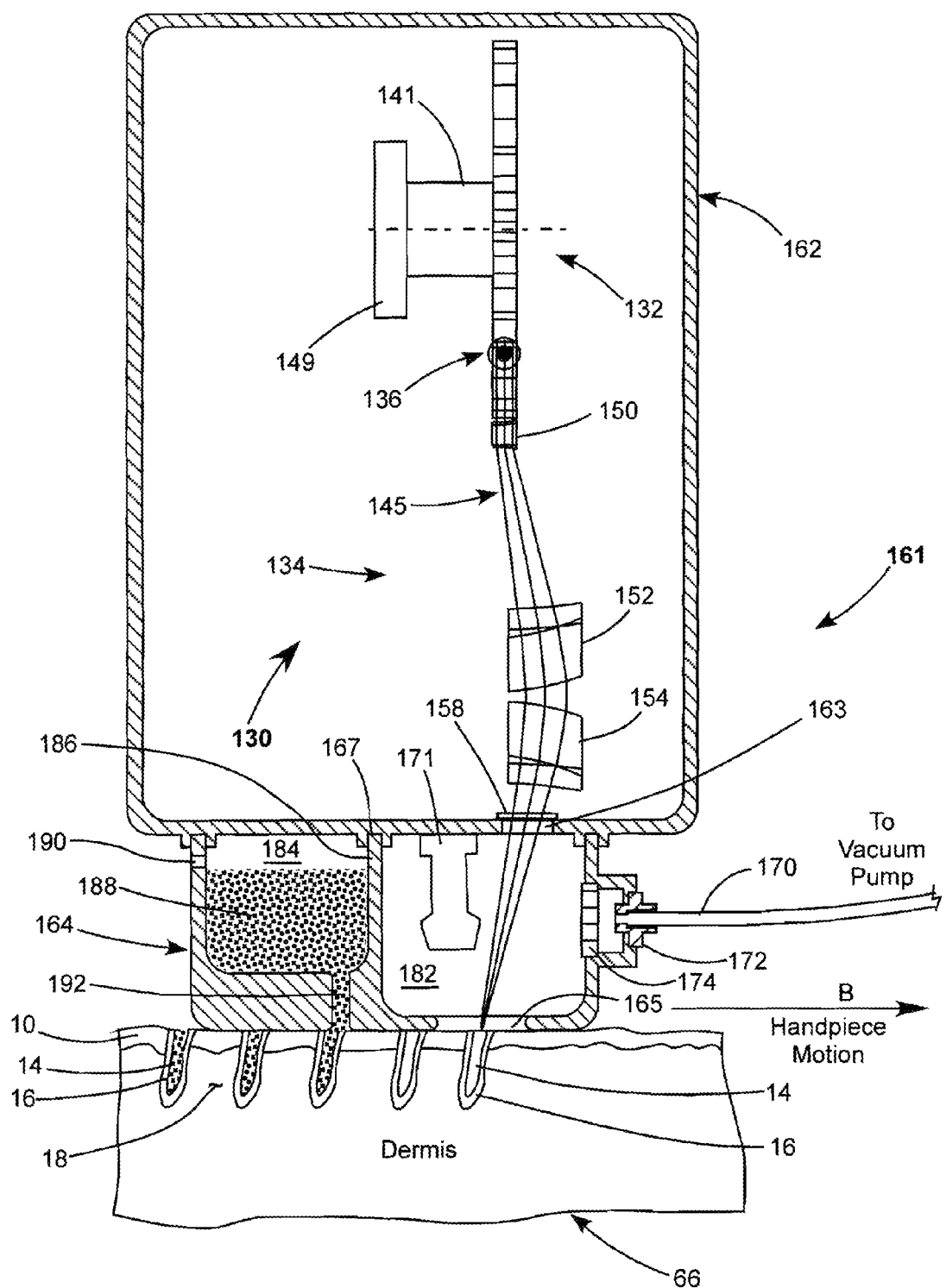
FIG. 11 schematically illustrates one example of a handpiece including the apparatus of FIGS. 9A-C, the handpiece including a removable tip connectable to a vacuum pump for exhausting smoke and ablation debris from the path of the laser beam.

FIG. 11 schematically illustrates one embodiment of a handpiece 161 or applicator in accordance with the present invention including an example of above described apparatus 130. Handpiece 161 is depicted irradiating a fragment 166 of skin being treated. The handpiece is moved over the skin being treated, as indicated by arrow B, with tip 164 in contact with the skin. The irradiation provides parallel spaced-apart rows of above-described spaced-apart voids 14, only end ones of which are visible in FIG. 8. Spacing between the rows of spots may be narrower or broader than that depicted in FIG. 8, the spacing, here, being selected for convenience of illustration. Control of the row spacing can be affected by controlling delivery of the laser beam by optical motion sensor 171, or alternatively a mechanical motion sensor (mechanical mouse), as is known in the art. A description of such motion sensing and control is not necessary for understanding principles of the present invention and accordingly is not presented here. Descriptions of techniques for controlling delivery of a pattern of laser spots are provided in U.S. patent application Ser. No. 10/888,356 entitled "Method and Apparatus for fractional photo therapy of skin" and No. 11/020,648 entitled "Method and apparatus for monitoring and controlling laser-induced tissue treatment," the complete disclosures of which are hereby incorporated herein by reference.

In a preferred method of operation, apparatus 130 is housed in handpiece or applicator 161 including a housing 162 to which is attached an open-topped, removable tip 164, which is attached to the housing via slots 167. Pins and/or screws can also be used for this purpose. When tip 164 is attached to housing the tip is divided into two chambers 182 and 184 having no gas-passage therebetween. An aperture 163 in housing 162 is covered by window 158 such that optical access to chamber 182 is provided while preventing gas passage between the housing and chamber 182. In use, the base of the tip makes a reasonable gas-tight seal with the skin.

Laser beam 136 is directed into housing 162 via an articulated arm (not shown). Articulated arms for delivery infra red laser radiation are well known in the art. One preferred articulated arm is described in U.S. Patent Application No. 60/752,850 filed Dec. 21, 2005 entitled "Articulated arm for delivering a laser beam," the complete disclosure of which is hereby incorporated herein by reference. The focused beam 145 from lens 134 exits housing 162 via exit window 158, (here attached to the housing) and via aperture 163 in the housing, then passes through chamber 182 of tip 164 exiting via aperture 165 therein. A vacuum pump (not shown) is connected to removable tip 164 via a hose or tube 170. Tube 170 is connected to tip 164 via a removable and replacable adaptor 172. Operating the vacuum pump with tip 164 in contact with the skin creates negative pressure (partial vacuum) inside the tip. This withdraws smoke resulting from the laser ablation from the path of the laser beam, and draws debris products of the ablation away from window 158 in the housing. A filter element 174 in a wall of tip 164 prevents debris from being drawn into vacuum hose 170 and eventually into the pump.

The arrangement of the tip provides that, when the vacuum pump is operated, there is also negative pressure created in any void that is under the aperture. The seal of the base of the tip to the skin retains the negative pressure in voids over which the tip has passed. Chamber 184 of tip 164 serves as a reservoir for a mixture of stem cells and differentiating medium 188. A channel though the tip, from chamber 184 through the base of the tip, allows a flow of the stem-cell mixture into the voids. An aperture 190 through the tip allows gas to enter chamber 184 to assist in the free flow of the mixture through channel 192. It is also possible to supply positive pressure through such an aperture to further encourage flow of the mixture, where pressure is measured relative to the ambient pressure outside of the apparatus. Alternatively, the stem cells can be applied topically following laser irradiation without the assistance of vacuum or positive pressure.

EXAMPLES

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Micropore Channel Creation

Freshly excised human skin samples are irradiated with a 30W, 10.6 μm $CO_2$ laser at varying pulse energies. The laser beams carried a near diffraction limited $1/e^2$ Gaussian spot size of approximately 120 μm, with pulse energies ranging from 8 to 20 mJ that are delivered through an apparatus capable of a repetition rate up to 1500 spots/second.

The skin is heated on a digital hot plate (Cole-Parmer Instrument Co., Vernon Hills, Ill.), and the skin surface temperature is measured with a Mintemp MT4 infrared probe (Raytek Corporation, Santa Cruz, Calif.). The laser treatment is initiated when the skin surface reaches a temperature of 98±3° F. The laser handpiece is translated at a specific velocity by using a precision linear stage driven by an ESP 300 motion controller (Newport Co., Irvine, Calif.). The firing rate of the laser is automatically adjusted by the laser handpiece to produce a specific density of lesions. A single pass is made at a constant velocity of 1.0 cm/s and spot density of 400 microscopic ablative treatment zones per $cm^2$ creating an interlesional distance of approximately 500 μm. The voids thus created are about 200 μm to 4 mm in depth.

Example 2

Treatment with Stem Cells

Figure 12:
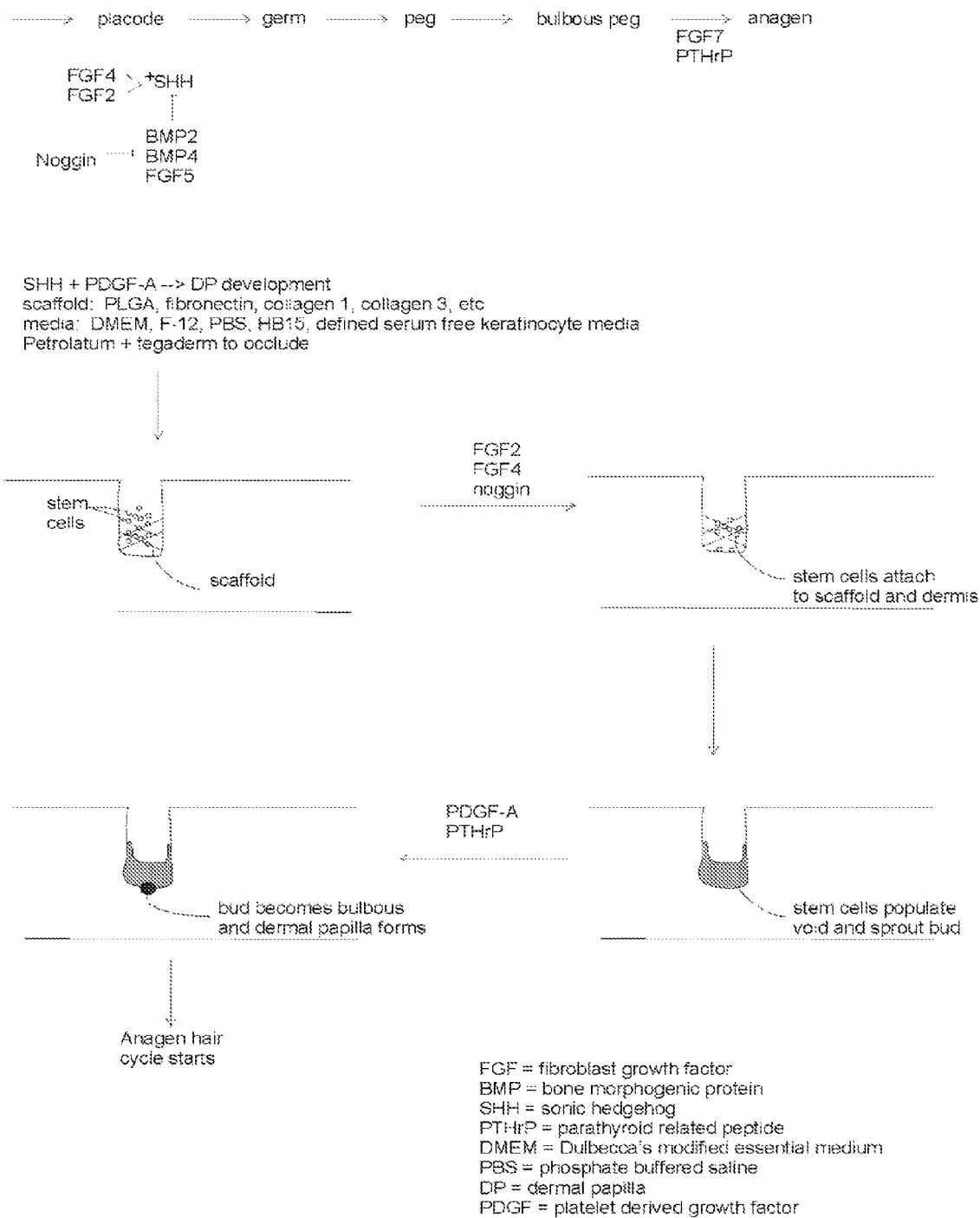
FIG. 12 illustrates the morphogenesis of hair follicle and one aspect of the invention where stem cells, scaffold, and differentiation factor are placed in a micropore channel created using laser irradiation of the skin.

Into the base of the microchannel pores or voids created in Example 1 is placed a solution containing hair follicle stem cells and PLGA that acts as a scaffold (FIG. 12). Hair follicle placod formation is promoted by using serum free media containing fibroblast growth factor (FGF2 ad/or FGF4) or noggin at a concentration of about 20 ng/mL. The stem cells attach to the scaffold and the dermis. The FGF and/or noggin treatment is continued for 2-3 days until the stem cells populate the microchannel pore and sprout a bud. The development of the bud into a dermal papilla requires the activity of sonic hedgehog (SHH) and platelet derived growth factor-A (PDGF-A). Therefore, the bud is exposed to media containing PDGF-A and/or PTHrP at a concentration of about 17 ng/mL.

Finally, anagen is initiated by the replacement of the media with a serum free media containing FGF7 (25 ng/ml). This allows the hair to begin to grow and cycle similar to a normal hair (FIG. 12).

Those skilled in the art may devise other contamination reducing methods or devices without departing from the spirit and scope of the present invention.

In summary, the present invention is described above in terms of a preferred and other embodiments. The invention is not limited, however, to the embodiments described and depicted. Rather, the invention is limited only by the claims appended hereto.

All printed patents and publications referred to in this application are hereby incorporated herein in their entirety by this reference.

What is claimed is:

1. An apparatus comprising:
   a handpiece movable over skin, the handpiece arranged to receive an optical beam having an absorption coefficient in water of about 100 $cm^{-1}$ to 12,300 $cm^{-1}$, the handpiece configured to focus the optical beam at a plurality of spaced-apart locations on the skin with a pulse energy per location of 5 mJ to 40 mJ thereby creating a plurality of voids in the skin for the deposition of a composition, wherein the composition comprises a stem cell and a growth media, and the handpiece is configured to focus the optical beam to create voids with a depth of about 200 μm to 4 mm, with a density of 200 to 4000 voids per $cm^2$ per pass, at a rate of 100 per second to 5000 per second, and such that viable tissue separating adjacent voids has a width, at a narrowest point thereof, between about 50 μm and 500 μm.

2. The apparatus of claim 1, further comprising an applicator arranged to deposit the composition in the voids following the formation of the voids.

3. The apparatus of claim 2, wherein the applicator further comprises a removable tip that attaches to the handpiece.

4. The apparatus of claim 1, wherein the composition further comprises a scaffold.

5. The method of claim 4, wherein the scaffold is selected from the group consisting of poly(lactic-co-glycolic acid) (PLGA), fibronectin, collagen 1, and collagen 3.

6. The apparatus of claim 1, wherein the stem cell is hair follicle cell.

7. The apparatus of claim 6, wherein the composition further comprises a melanocyte stem cell.

8. The apparatus of claim 1, wherein the media comprises a proliferation-inducing growth factor.

9. The apparatus of claim 8, wherein the growth factor is selected from the group consisting of epidermal growth factor (EGF), amphiregulin, acidic fibroblast growth factor (aFGF or FGF-1), basic fibroblast growth factor (bFGF or FGF-2), and transforming growth factor alpha (TGFα), or combinations thereof.

10. The apparatus of claim 1, wherein the composition further comprises a hair-follicle differentiation factor.

11. The apparatus of claim 10, wherein the differentiation factor is selected from the group consisting of FGF2, FGF4, noggin, platelet-derived growth factor (PDGF), and parathyroid hormone-related protein (PTHrp), or combinations thereof.

12. The apparatus of claim 1, wherein the stem cell is a hair follicle cell.

13. The apparatus of claim 12, wherein the scanner is configured to rotate.

14. The apparatus of claim 12, wherein the scanner comprises one or more galvanometer scanners.

15. The apparatus of claim 1, wherein the optical beam is emitted by a laser.

16. The apparatus of claim 15, wherein the laser is a $CO_2$ laser with a wavelength of about 10.6 μm.

17. The apparatus of claim 1, further comprising a vacuum that removes debris that is removed from the skin during creation of the voids.

18. The apparatus of claim 1, further comprising a system that creates a positive pressure in a chamber containing the composition.

19. The apparatus of claim 1, wherein the voids are elongated.

* * * * *

UNITED STATES PATENT AND TRADEMARK OFFICE
CERTIFICATE OF CORRECTION

| | |
|---|---|
| PATENT NO. | : 8,208,189 B2 |
| APPLICATION NO. | : 12/102739 |
| DATED | : June 26, 2012 |
| INVENTOR(S) | : Basil M. Hantash et al. |

It is certified that error appears in the above-identified patent and that said Letters Patent is hereby corrected as shown below:

At column 3, line number 66, change "thryootropin" to --thyrotropin--.

At column 4, line number 16, change "comprising" to --comprise--.

At column 5, line number 40, after "include", insert --,--.

At column 6, line number 34, change "includes" to --include--.

At column 7, line number 2, change "cell" to --cells-- and at line number 23, change "cultures" to --culture--.

At column 9, line number 32, change "limited, to" to --limited to,--.

At column 10, line number 31, after "skin", delete "immediately after".

At column 11, line number 25, after "region", delete "of" and at line number 39, change "sites" to --site-- and at line number 62, after "process", delete "healing".

At column 12, line number 50, change the first occurrence of "cells" to --cell--.

At column 15, line number 11, after "of", delete "the" and at line number 64, change "principle" to --principal--.

At column 17, line number 8, change "principle" to --principal-- and at line number 19, change "passes" to --pass-- and at line number 46, after "to", insert --be--.

At column 18, line number 3, change "or" to --of-- and at line number 16, change "he" to --the-- and at line number 47, after "with" delete "the".

Signed and Sealed this
Fourteenth Day of August, 2012

David J. Kappos
*Director of the United States Patent and Trademark Office*

At column 19, line number 22, after "delivery" insert --of--.

In the Claims:

At column 21, claim number 6, line number 22, after "is" insert --a--.

At column 22, line number 11, replace claim 12 in its entirety with the following, as submitted in the February 7, 2012 Amendment and allowed by the Examiner:

--The apparatus of claim 1, further comprising a scanner configured to receive the optical beam and focus the optical beam at the plurality of spaced-apart locations on the skin.--

At column 20, line number 37, change "ad" to --and--.